(12) United States Patent
Moskowitz et al.

(10) Patent No.: US 10,028,740 B2
(45) Date of Patent: Jul. 24, 2018

(54) SPINAL FUSION IMPLANT WITH CURVILINEAR NAIL-SCREWS

(71) Applicant: Nathan C. Moskowitz, Rockville, MD (US)

(72) Inventors: Nathan C. Moskowitz, Rockville, MD (US); Mosheh T. Moskowitz, Rockville, MD (US); Ahmnon D. Moskowitz, Rockville, MD (US)

(73) Assignee: Moskowitz Family LLC, Rockville, MD (US)

( * ) Notice: Subject to any disclaimer, the term of this patent is extended or adjusted under 35 U.S.C. 154(b) by 0 days.

(21) Appl. No.: 15/862,016

(22) Filed: Jan. 4, 2018

(65) Prior Publication Data

US 2018/0125483 A1     May 10, 2018

Related U.S. Application Data

(63) Continuation of application No. 12/957,776, filed on Dec. 1, 2010, now Pat. No. 9,888,918, which is a
(Continued)

(51) Int. Cl.
*A61B 17/70* (2006.01)
*A61B 17/064* (2006.01)
(Continued)

(52) U.S. Cl.
CPC ........ *A61B 17/0642* (2013.01); *A61B 17/068* (2013.01); *A61B 17/7001* (2013.01);
(Continued)

(58) Field of Classification Search
CPC ........ A61B 17/7001–17/7046; A61B 17/7056; A61B 17/7053; A61B 17/8625; A61B 17/86; A61B 2017/8655
See application file for complete search history.

(56) References Cited

U.S. PATENT DOCUMENTS 2,430,293 A    11/1947  Howells
4,013,207 A     3/1977  ErkenBrack
(Continued)

FOREIGN PATENT DOCUMENTS

WO    2004093749    11/2004
WO    2006091503     8/2006

OTHER PUBLICATIONS

Vincent C. Traynelis, "Prosthetics and Biologics: The Wave of the Future," Clinical Neurosurgery, vol. 50, Proceedings of the Congress of Neurological Surgeons, Philadelphia, PA 2002, Chapter 9, pp. 207-219.
(Continued)

*Primary Examiner* — Jacqueline Johanas
(74) *Attorney, Agent, or Firm* — Fish & Richardson P.C.

(57) ABSTRACT

A horizontal-transvertebral curvilinear nail-screw (HTCN) including a body portion having a first end and a second end, wherein the first end is opposed to the second end; and a head at the first end of the body portion, wherein the body portion has a predetermined curvilinear shape and includes a pointed tip at the second end of the body portion, and a method of surgically implanting universal horizontal-transvertebral curvilinear nail-screws (HTCN) into a plurality of adjacent vertebrae.

23 Claims, 33 Drawing Sheets

Related U.S. Application Data continuation-in-part of application No. 12/471,340, filed on May 22, 2009, now Pat. No. 8,734,516, which is a continuation-in-part of application No. 12/054,335, filed on Mar. 24, 2008, now Pat. No. 7,972,363, which is a continuation-in-part of application No. 11/842,855, filed on Aug. 21, 2007, now Pat. No. 7,942,903, which is a continuation-in-part of application No. 11/536,815, filed on Sep. 29, 2006, now Pat. No. 7,846,188, which is a continuation-in-part of application No. 11/208,644, filed on Aug. 23, 2005, now Pat. No. 7,704,279.

(60) Provisional application No. 60/670,231, filed on Apr. 12, 2005, provisional application No. 61/265,752, filed on Dec. 1, 2009.

(51) Int. Cl.
*A61B 17/86* (2006.01)
*A61B 17/068* (2006.01)
*A61F 2/44* (2006.01)

(52) U.S. Cl.
CPC ...... *A61B 17/7004* (2013.01); *A61B 17/7011* (2013.01); *A61B 17/7023* (2013.01); *A61B 17/8605* (2013.01); *A61B 17/8625* (2013.01); *A61B 17/8685* (2013.01); *A61B 2017/0641* (2013.01); *A61B 2017/0647* (2013.01); *A61B 2017/0648* (2013.01); *A61F 2/4455* (2013.01); *A61F 2220/0025* (2013.01)

(56) References Cited

U.S. PATENT DOCUMENTS

| | | | |
|---|---|---|---|
| 4,135,506 A * | 1/1979 | Ulrich | A61B 17/8872 606/207 |
| 4,165,597 A | 8/1979 | Scanland et al. | |
| 4,274,401 A | 6/1981 | Miskew | |
| 4,554,914 A | 11/1985 | Kapp et al. | |
| 4,599,086 A | 7/1986 | Doty | |
| 4,636,217 A | 1/1987 | Ogilvie et al. | |
| 4,790,303 A | 12/1988 | Steffee | |
| 4,960,420 A | 10/1990 | Goble et al. | |
| 4,997,432 A | 3/1991 | Keller | |
| 5,062,850 A | 11/1991 | MacMillan et al. | |
| 5,123,926 A | 6/1992 | Pisharodi | |
| 5,290,312 A | 3/1994 | Kojimoto et al. | |
| 5,405,391 A | 4/1995 | Henderson et al. | |
| 5,514,180 A | 5/1996 | Heggeness et al. | |
| 5,609,593 A | 3/1997 | Errico et al. | |
| 5,660,188 A | 8/1997 | Groiso | |
| 5,667,472 A | 9/1997 | Finn et al. | |
| 5,782,832 A | 7/1998 | Larsen et al. | |
| 5,865,848 A | 2/1999 | Baker | |
| 5,888,223 A | 3/1999 | Bray, Jr. | |
| 5,960,522 A | 10/1999 | Boe | |
| 6,126,689 A | 10/2000 | Brett | |
| 6,342,074 B1 | 1/2002 | Simpson | |
| 6,368,350 B1 | 4/2002 | Erickson et al. | |
| 6,375,682 B1 | 4/2002 | Fleischmann et al. | |
| 6,419,704 B1 | 7/2002 | Ferree | |
| 6,432,106 B1 | 8/2002 | Fraser | |
| 6,458,159 B1 | 10/2002 | Thalgott | |
| 6,471,707 B1 | 10/2002 | Miller et al. | |
| 6,527,804 B1 | 3/2003 | Gauchet et al. | |
| 6,533,818 B1 | 3/2003 | Weber et al. | |
| 6,558,386 B1 | 5/2003 | Cragg | |
| 6,558,423 B1 | 5/2003 | Michelson | |
| 6,572,653 B1 | 6/2003 | Simonson | |
| 6,579,318 B2 | 6/2003 | Varga et al. | |
| 6,582,468 B1 | 6/2003 | Gauchet | |
| 6,629,998 B1 | 10/2003 | Lin | |
| 6,641,614 B1 | 11/2003 | Wagner et al. | |
| 6,652,527 B2 | 11/2003 | Zucherman et al. | |
| 6,689,125 B1 | 2/2004 | Keith et al. | |
| 6,719,794 B2 | 4/2004 | Gerber | |
| 6,723,126 B1 | 4/2004 | Berry | |
| 6,733,532 B1 | 5/2004 | Gauchet et al. | |
| 6,764,491 B2 | 7/2004 | Frey et al. | |
| 6,770,094 B2 | 8/2004 | Fehling et al. | |
| 6,824,564 B2 | 11/2004 | Crozet | |
| 6,904,308 B2 | 6/2005 | Frisch et al. | |
| 6,953,477 B2 | 10/2005 | Berry | |
| 6,955,671 B2 | 10/2005 | Uchikubo | |
| 6,972,019 B2 | 12/2005 | Michelson | |
| 7,030,904 B2 | 4/2006 | Adair et al. | |
| 7,033,394 B2 | 4/2006 | Michelson | |
| 7,037,258 B2 | 5/2006 | Chatenever et al. | |
| 7,097,615 B2 | 8/2006 | Banik et al. | |
| 7,211,112 B2 | 5/2007 | Baynham et al. | |
| 7,326,248 B2 | 2/2008 | Michelson | |
| 7,442,209 B2 | 10/2008 | Michelson | |
| 7,713,289 B2 | 5/2010 | Matthys | |
| 7,862,616 B2 | 1/2011 | Lechmann et al. | |
| 7,879,036 B2 | 2/2011 | Biedermann et al. | |
| 7,909,871 B2 * | 3/2011 | Abdou | A61B 17/70 606/246 |
| 8,105,362 B2 | 1/2012 | Duarte | |
| 8,328,872 B2 | 12/2012 | Duffield et al. | |
| 8,357,198 B2 | 1/2013 | McGraw et al. | |
| 8,403,986 B2 | 3/2013 | Michelson | |
| 8,617,245 B2 * | 12/2013 | Brett | A61F 2/442 623/17.16 |
| 8,951,295 B2 | 2/2015 | Matityahu et al. | |
| 9,011,497 B2 * | 4/2015 | Ben-Arye | A61B 17/70 606/246 |
| 9,427,270 B2 * | 8/2016 | Housman | A61B 17/8625 |
| 2001/0021852 A1 | 9/2001 | Chappius | |
| 2002/0068977 A1 | 6/2002 | Jackson | |
| 2002/0143338 A1 | 10/2002 | Orbay et al. | |
| 2003/0181913 A1 * | 9/2003 | Lieberman | A61B 17/1604 606/325 |
| 2004/0088054 A1 | 5/2004 | Berry | |
| 2004/0177531 A1 | 9/2004 | DiBenedetto et al. | |
| 2004/0254644 A1 | 12/2004 | Taylor | |
| 2005/0027362 A1 | 2/2005 | Williams et al. | |
| 2005/0049590 A1 | 3/2005 | Alleyne et al. | |
| 2005/0177235 A1 | 8/2005 | Baynham et al. | |
| 2005/0216084 A1 | 9/2005 | Fleischmann | |
| 2005/0273170 A1 | 12/2005 | Navarro et al. | |
| 2005/0278026 A1 | 12/2005 | Gordon et al. | |
| 2007/0213820 A1 | 9/2007 | Magerl et al. | |
| 2008/0033432 A1 * | 2/2008 | McGraw | A61B 17/70 606/86 A |
| 2008/0045951 A1 | 2/2008 | Fanger et al. | |
| 2008/0188896 A1 | 8/2008 | Sevrain | |
| 2009/0105831 A1 | 4/2009 | Jones et al. | |
| 2010/0016903 A1 * | 1/2010 | Matityahu | A61B 17/866 606/301 |
| 2010/0094346 A1 | 4/2010 | Matityahu | |
| 2010/0145460 A1 | 6/2010 | McDonough et al. | |
| 2010/0211108 A1 | 8/2010 | Lemole | |

OTHER PUBLICATIONS

E.K. Wai et al.. "Disk Replacement Arthroplasties: Can the Success of Hip and Knee Replacements be Repeated in the Spine?." Seminars in Spine Surgery, vol. 15, No. 4 (Dec. 2003), pp. 473-482.

Richard D. Guyer et al., "Intervertebral Disc Prostheses," Spine Journal, vol. 28, No. 15S, Supp. to Aug. 1, 2003, pp. S15-S23.

Dieter Grob et al., "Clinical Experience With the Dynesys Semirigid Fixation System for the Lumbar Spine," Spine, vol. 30, No. 3, 2005, pp. 324-331.

International Search Report (ISR) and Written Opinion of the International Searching Authority, dated Dec. 3, 2007, International Application No. PCT/US 07/05005.

International Search Report (ISR) and Written Opinion of the International Searching Authority, dated May 21, 2008, International Application No. PCT/US2007/021015.

(56) References Cited

OTHER PUBLICATIONS

International Search Report (ISR) and Written Opinion of the International Searching Authority, dated Jul. 9, 2008, International Application No. PCT/US2007021013.

* cited by examiner

SPINAL FUSION IMPLANT WITH CURVILINEAR NAIL-SCREWS

This application is a Continuation of application Ser. No. 12/957,776 filed Dec. 1, 2010, which is a Continuation-In-Part of application Ser. No. 12/471,340 filed on May 22, 2009, now U.S. Pat. No. 8,734,516 issued May 27, 2014, which is a Continuation-In-Part of application Ser. No. 12/054,335 filed on Mar. 24, 2008, now U.S. Pat. No. 7,972,363 issued Jul. 5, 2011, which is a Continuation-In-Part of application Ser. No. 11/842,855 filed Aug. 21, 2007, now U.S. Pat. No. 7,942,903 issued May 17, 2011, which is a Continuation-In-Part of application Ser. No. 11/536,815 filed Sep. 29, 2006, now U.S. Pat. No. 7,846,188 issued Dec. 7, 2010, and Ser. No. 12/957,776 filed Dec. 1, 2010, claims priority under 35 U.S.C. § 119(e) of U.S. Provisional Application No. 60/670,231, filed on Apr. 12, 2005, and U.S. Provisional Application No. 61/265,752, filed on Dec. 1, 2009; the entire contents of all the above identified patent applications are hereby incorporated by reference in their entirely.

FIELD OF DISCLOSURE

The present invention relates to a unique universal horizontal-transvertebral curvilinear nail-screw (HTCN) and to a method of applying such an HTCN to the spine, whereby a series of HTCN's, according to the exemplary embodiments, can be implanted into adjacent vertebrae can be inter-connected with either rigid or flexible jointed rods, fusing two or more adjacent vertebral bodies together thereby achieving either rigid or flexible fusion, respectively, and thus obviating the need for pedicle screw fixation in many but not all cases. The exemplary embodiments also can be used to salvage and/or extend pre-existing pedicle screw fusions.

BACKGROUND

The history and evolution of instrumented spinal fusion in the entire human spine has been reviewed in related application Ser. No. 12/054,335 filed on Mar. 24, 2008, Ser. No. 11/842,855, filed on Aug. 21, 2007, Ser. No. 11/536,815 filed on Sep. 29, 2006, and Ser. No. 11/208,644 filed on Aug. 23, 2005, the contents of which are hereby incorporated by reference in their entirety. Conventionally, the majority of posterior and anterior spinal fusion surgical techniques are typically supplemented with the posterior placement of adjacent vertebral trans-pediclar screws.

Complications of pedicle screw placement in the spine include misplaced screws with neural and/or vascular injury, excessive blood loss, prolonged recovery, incomplete return to work, and excessive rigidity leading to adjacent segmental disease requiring further fusions and re-operations. Recent advances in pedicle screw fixation including minimally invasive, and stereotactic CT image-guided technology, imperfectly address some but not all of these issues.

SUMMARY

The present invention recognizes the aforementioned problems with conventional apparatus and solves these problems.

Herein described are exemplary embodiments of novel HTCNs which are implanted and embedded within adjacent vertebral bodies using a lateral horizontal side-to-side-trajectory avoiding the pedicles entirely, and thereby avoiding all the risks associated with the placement of transpedicular vertebral screws. Direct non-trans-pedicular placement of HTCNs into the vertebral bodies, according to the exemplary embodiments, is possible because the HTCN is curved, and thus, can achieve horizontal transvertebral access, which is not possible by conventional straight screws/nails. Likewise, the inter-connection of HTCNs with either rigid rods, or multiple embodiments of jointed flexible rods, can achieve rigid or flexible fusion, respectively.

The exemplary embodiments of a Horizontal transvertebral curvilinear nails (HTCN) can provide a segmental vertebral spinal fusion having a strength that is equal to or greater than a strength of conventional pedicle screws without the complications arising from conventional pedicle screw placement, which include misplacement with potential nerve and/or vascular injury, violation of healthy facets, and possible pedicle destruction. By placing HTCNs horizontally across the vertebral body, and not into the vertebral bodies via the transpedicular route, thereby excluding the posterior spinal column, the exemplary embodiments can preserve healthy facet joints and pedicles. The exemplary embodiments of HTCNs are designed with predetermined curved angles to avoid laterally exiting nerve roots. Furthermore, with respect to patients who already have had pedicle screws, with concomitant pedicular destruction, placement of HTCNs according to the exemplary embodiments can be employed as a salvage procedure achieving segmental fixation without having to engage additional rostral and caudal vertebrae transpedicularly, unnecessarily lengthening a spinal fusion, and adding more operative risk per fused level.

Furthermore, as a result of the orientation and length of the HTCNs according to the exemplary embodiments, multiple level fusions can be easily performed.

For example, exemplary embodiments are directed to one or more HTCNs, one or more interconnecting rigid rods, and one or more interconnecting jointed flexible rods. The HTCN can include a nail/screw which is precurved in multiple angles (e.g., a plurality of predetermined angles), for example, that take into account a safe trajectory upon insertion into the lateral posterior vertebral body beneath the pedicle and spinal canal, through the transverse process (or lateral to it), whose entry point and trajectory avoids exiting/traversing nerve roots from the spinal canal. The connecting rod can include a solid rod which can achieve rigid fusion. The embodiments of the connecting rod can include one or more flexible rods. For example, the flexible rods can include side to side, or head to head ball-socket joints that can allow multiple degrees of freedom of movement. The exemplary embodiment of the rods can be locked onto rostral and caudal vertebral HTCNs via locking mechanisms. In an exemplary embodiment, all of the rods can be locked onto rostral and caudal vertebral HTCNs via locking mechanisms.

Another exemplary embodiment is directed to a method of inserting a HTCN laterally into the vertebral body. The method can include, for example, either direct, fluoroscopic, or navigational image guidance visualization of the transverse process to determine the initial entry point through the transverse process (or lateral, caudal or cephalad to it), and its curvilinear trajectory to the vertebral, lateral, sub-pedicular, sub-canalicular lateral entry point into the vertebral body.

Exemplary methods of interlocking sequential HTCNs with rigid or jointed rods and their interlocking connectors are described herein. Once the surgeon is satisfied with the position and placement of the HTCNs either in unilateral or bilateral adjacent vertebral bodies, interconnecting rods that are either rigid, or jointed, can be attached and locked to the HTCNs achieving rigid or flexible fusion depending on the need of the patient and the choice of the surgeon.

BRIEF DESCRIPTION OF THE DRAWINGS

The accompanying drawings are presented to aid in the description of embodiments of the invention and are provided solely for illustration of the embodiments and not limitation thereof.

DETAILED DESCRIPTION OF THE EXEMPLARY EMBODIMENTS OF THE INVENTION

Aspects of the invention are disclosed in the following description and related drawings directed to specific embodiments of the invention. Alternate embodiments may be devised without departing from the scope of the invention. Additionally, well-known elements of the invention will not be described in detail or will be omitted so as not to obscure the relevant details of the invention.

The word "exemplary" is used herein to mean "serving as an example, instance, or illustration." Any embodiment described herein as "exemplary" is not necessarily to be construed as preferred or advantageous over other embodiments. Likewise, the term "embodiments of the invention" does not require that all embodiments of the invention include the discussed feature, advantage or mode of operation.

With reference to FIGS. 1A-8D, exemplary embodiments of the invention will now be described.

1. The Medical Device

Referring to FIGS. 1A-8D, the above described problems of the conventional art can be solved in the spine by horizontal transvertebral insertion into adjacent vertebral bodies either unilateral or bilateral HTCN-interconnecting rigid or flexible jointed connecting constructs according to the exemplary embodiments, thereby achieving rigid or flexible vertebral fusion/fixation.

For example, FIGS. 1A-H illustrate three-dimensional views of five different exemplary embodiments of a single HTCN which can be horizontally inserted unilaterally into a single vertebra.

Figure 1A:
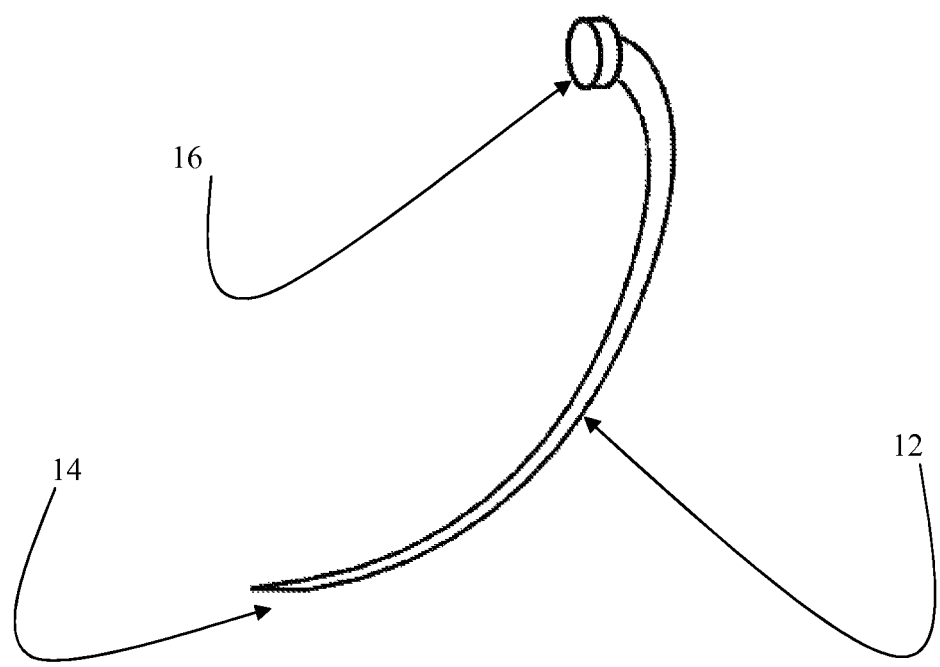
FIGS. 1A-H illustrate an exemplary embodiment of an HTCN solid-flat head embodiment I in lateral (Figure A), and en-face (Figure B) views, and lateral views of an exemplary embodiment of a threaded screw cap embodiment II (Figure C), an exemplary embodiment of a threaded nail body embodiment III (Figure D), an exemplary embodiment of a fish-hooked tail embodiment IV (Figures E and F), and an exemplary embodiment of a threaded tail/screw embodiment V (Figures G and H).
Figure 1B:
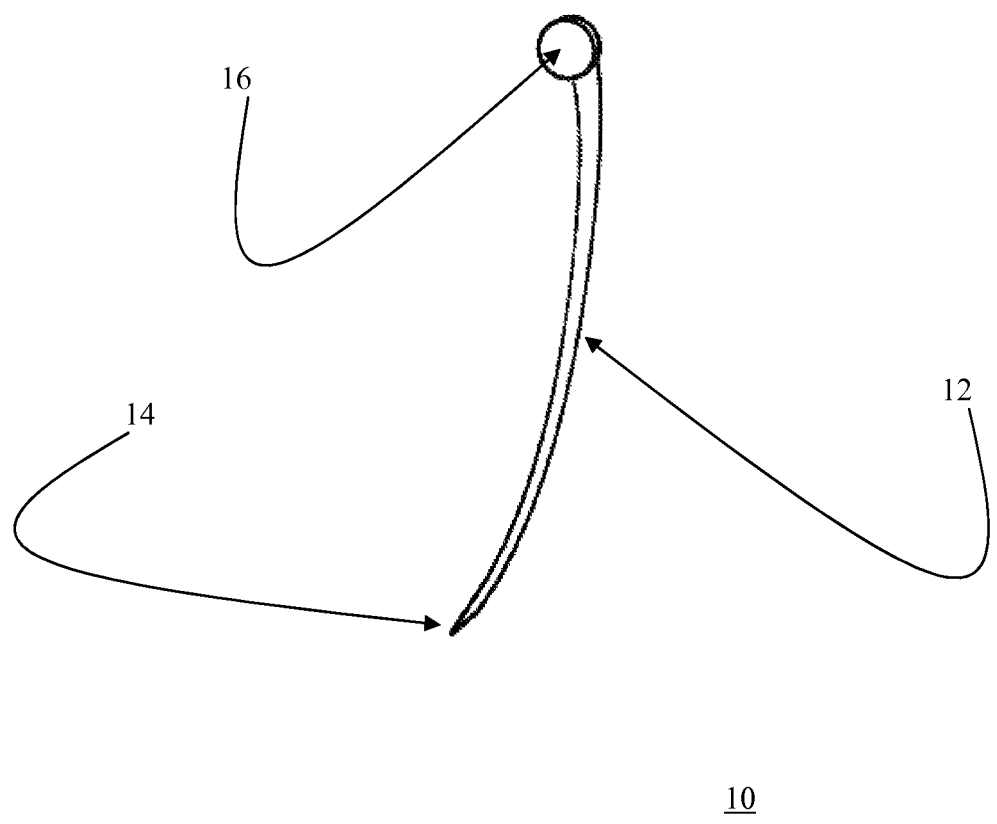

FIGS. 1A-B illustrate an exemplary embodiment of a solid flat-head HTCN 10 (embodiment I). The HTCN 10 can include a single piece construct manufactured out of any type of bio-compatible material. The HTCN 10 can include a body 12 having a sharp pointed tip 14 and a head 16. The HTCN 10 can include a geometry that is curvilinear, allowing its sharp pointed tip 14 to be posteriorly or laterally, or anteriorly introduced, and to penetrate the mid lateral aspect of a vertebral body. The head 16 can include a flat head that provides a surface which can be tamped upon by any variety of instruments in order to insert the pointed tip 14 (e.g., tail portion) and a portion of the body 12 into the core of the vertebral body. In this example, the orientation of the HTCN 10 within the vertebral body is horizontal, as opposed to trans-pedicular. Hence, the exemplary embodiment allows a non-pedicular based posterior, lateral or anterior vertebral fusion.

Figure 1C:
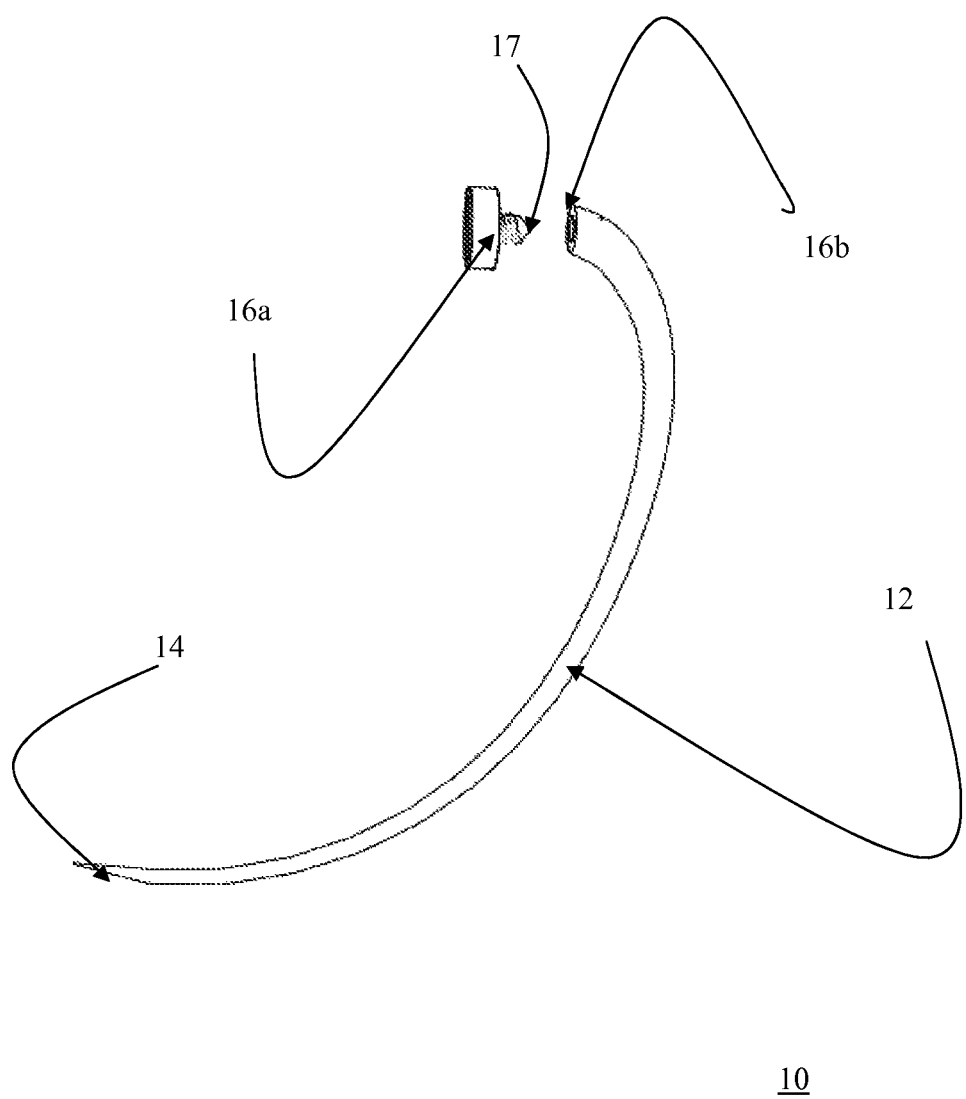

FIG. 1C illustrates an exemplary embodiment of an HTCN 10 having a threaded screw cap 16 (embodiment II). In this embodiment, the geometry of the HTCN 10 can be identical to the embodiment I described above. Rather than being one solid piece, the exemplary HTCN 10 can include two separate pieces or portions, such as a) a screw cap 16*a*, and b) the HTCN body 12 and portion (e.g., tail portion) with a pointed tip 14. The superior flat headed surface 16 of the HTCN 10 can include a central threaded perforation or opening 16*b* into which a threaded screw portion 17 of the cap 16*a* can be secured by threaded engagement or screwed into. The screw cap 16*a* can secure the HTCN 10 to the interconnecting rod locking devices (described in greater detail below).

Figure 1D:
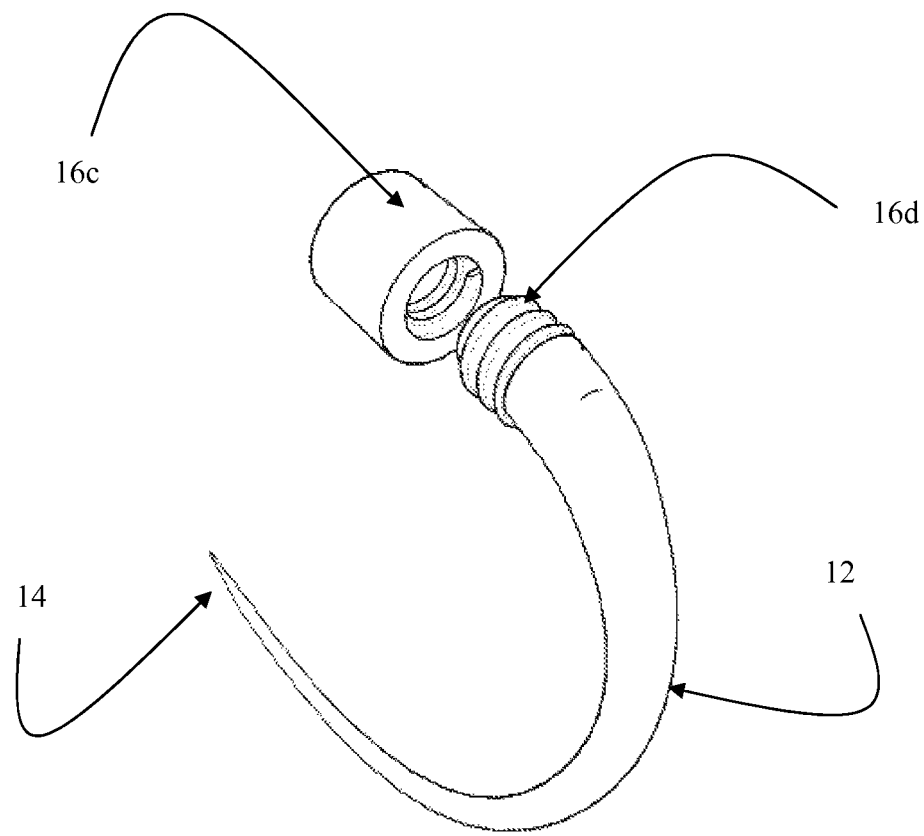

FIG. 1D illustrates an exemplary embodiment of an HTCN 10 having a body 12 includes a threaded head or portion 16*d* (embodiment III). In this embodiment, the upper outer surface of the head 16*d* is threaded to accept a screw cap 16*c* having internal corresponding threading. The HTCN 10 according to this embodiment can function similar to the embodiment II described above.

Figure 1E:
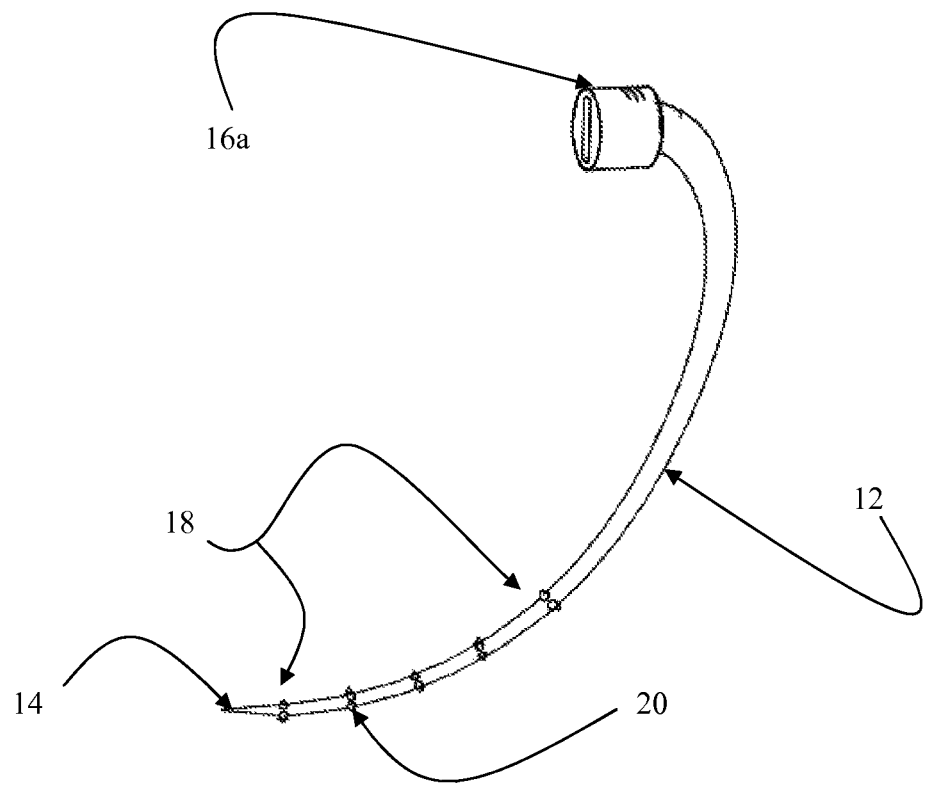
Figure 1F:
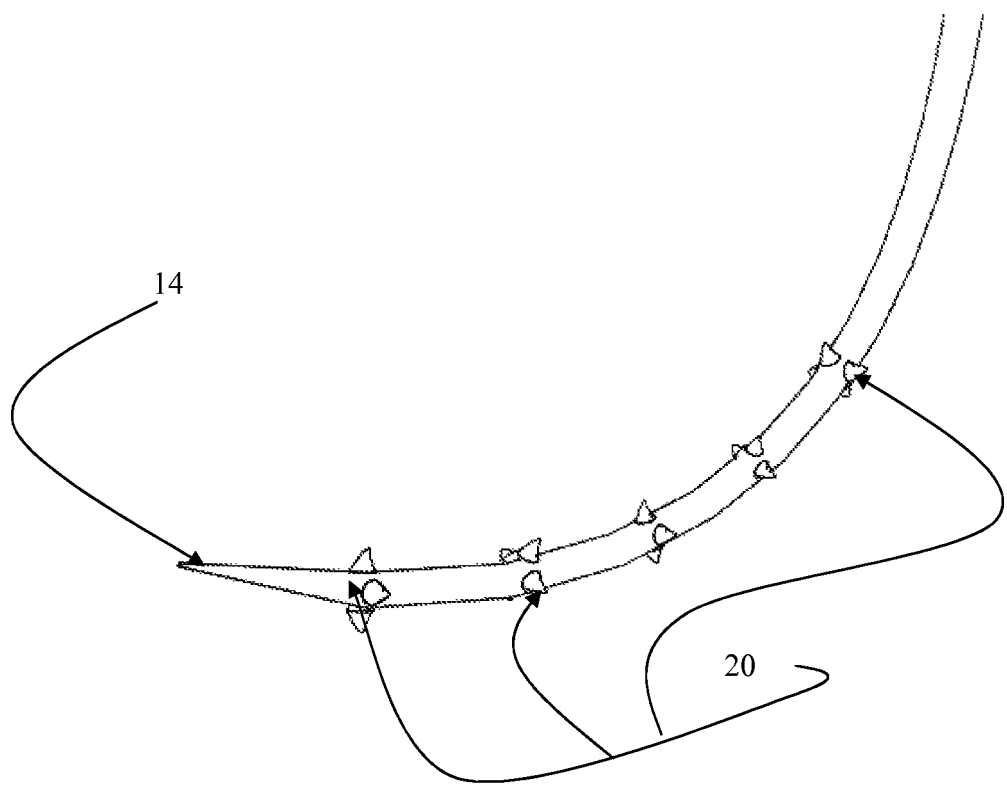

FIGS. 1E and F illustrate an exemplary embodiment of an HTCN 10 including a fish-hooked tail or portion 18 (embodiment IV). In this embodiment, the tail 18 of the HTCN 10 can include a series of radially arranged fish-hooks 20 to engage the cancellous core of the vertebral body. FIG. 1F is an enlargement illustrating details of an exemplary embodiment of the radial fish-hook 18.

Figure 1G:
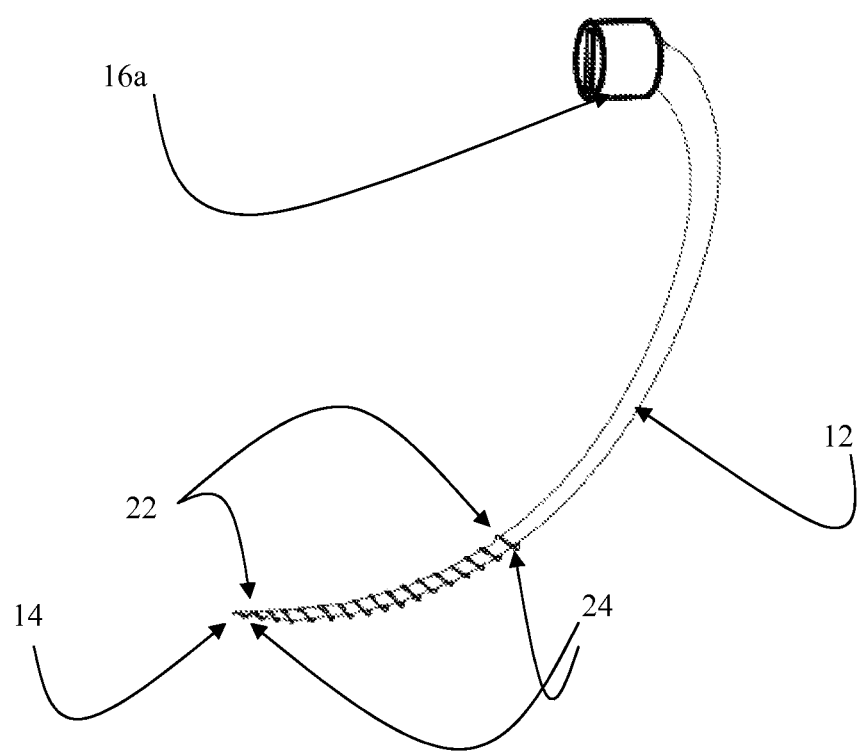
Figure 1H:
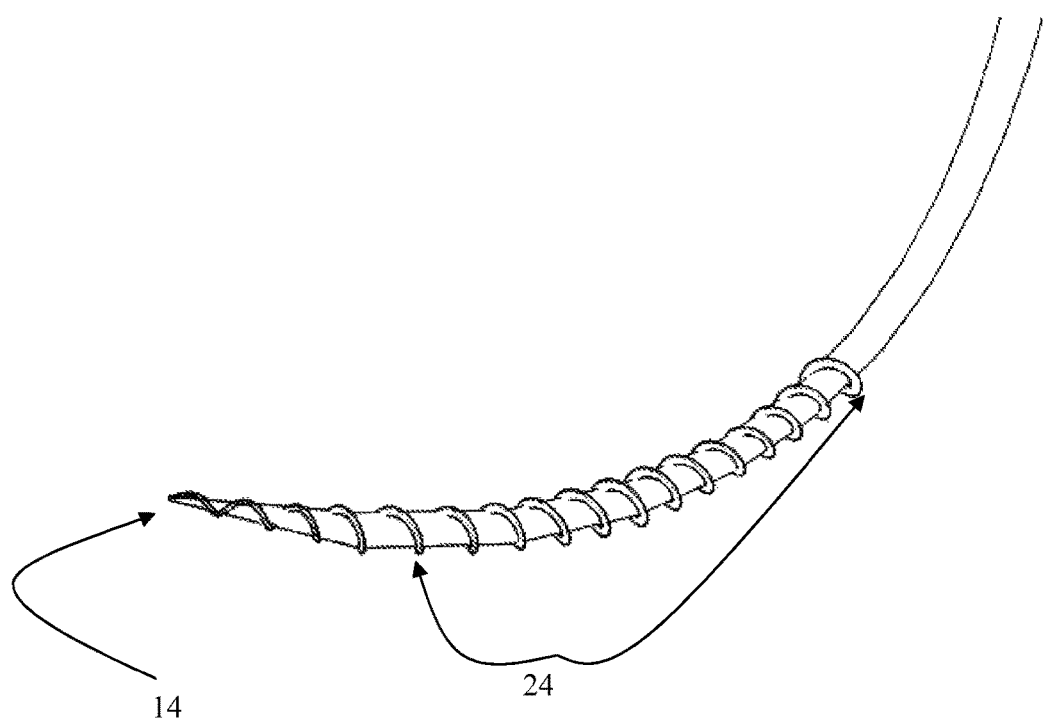
Figure 2A:
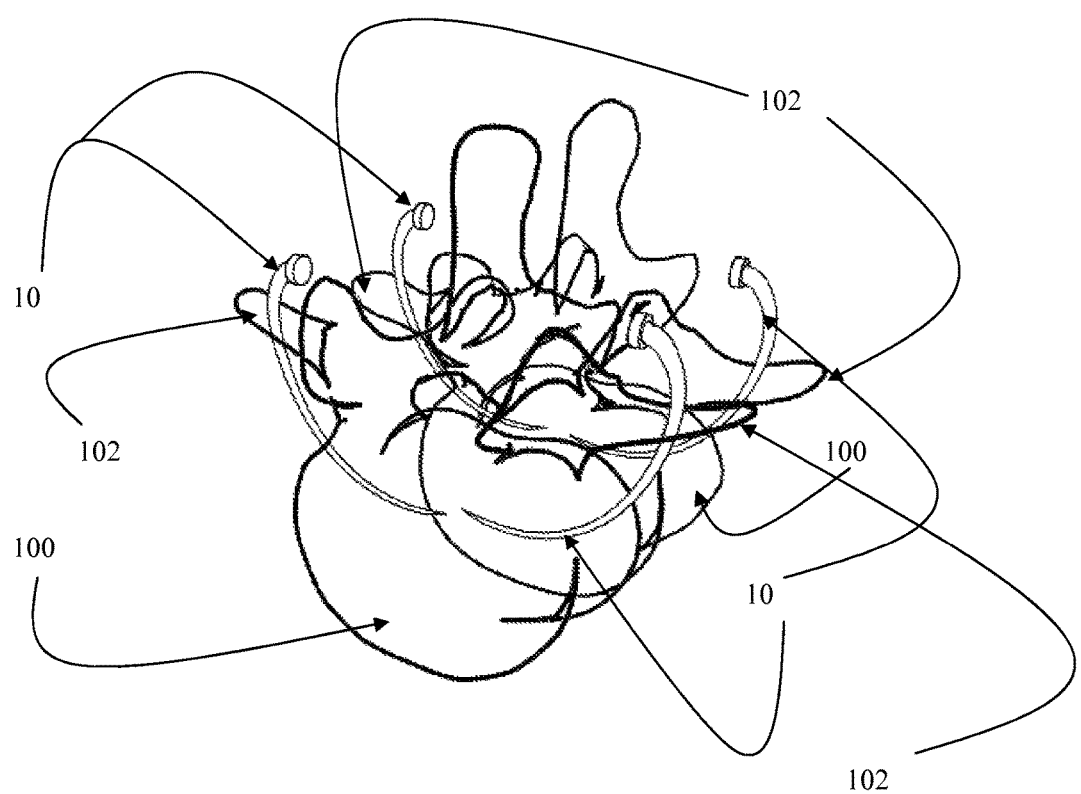
FIGS. 2A-D illustrate exemplary embodiments of an HTCN, embodiments (I-V), inserted bilaterally into two adjacent transparent vertebral bodies in top-oblique (Fig A), lateral (Figure B), axial (Figure C) and top (Figure D) views.
Figure 2B:
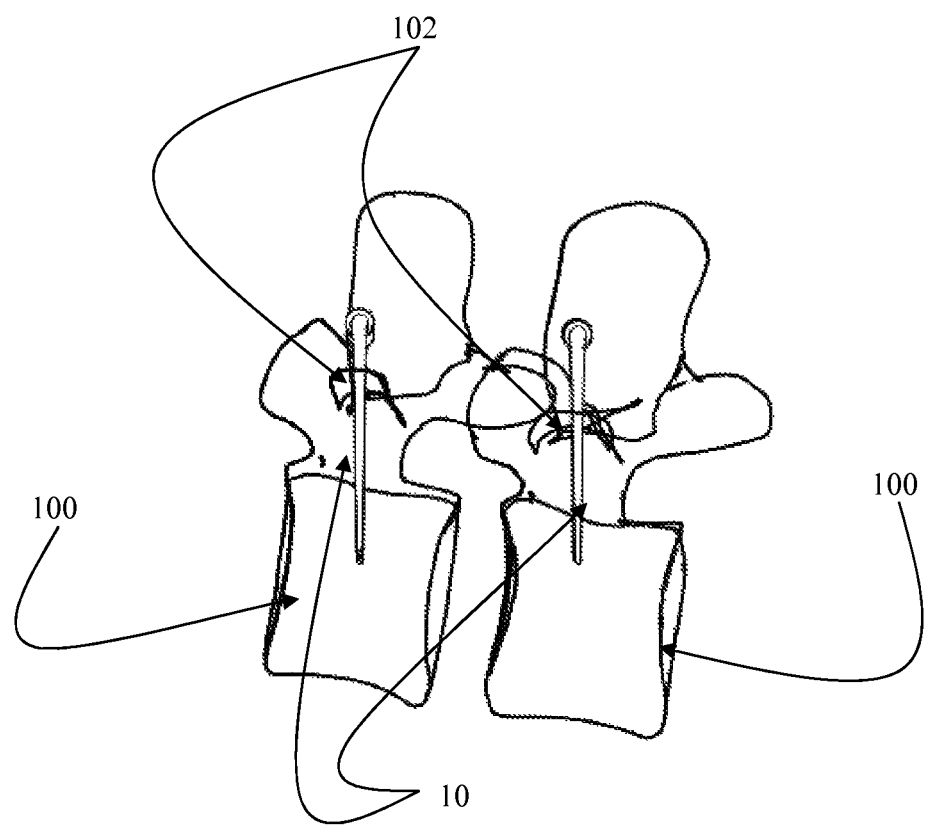
Figure 2C:
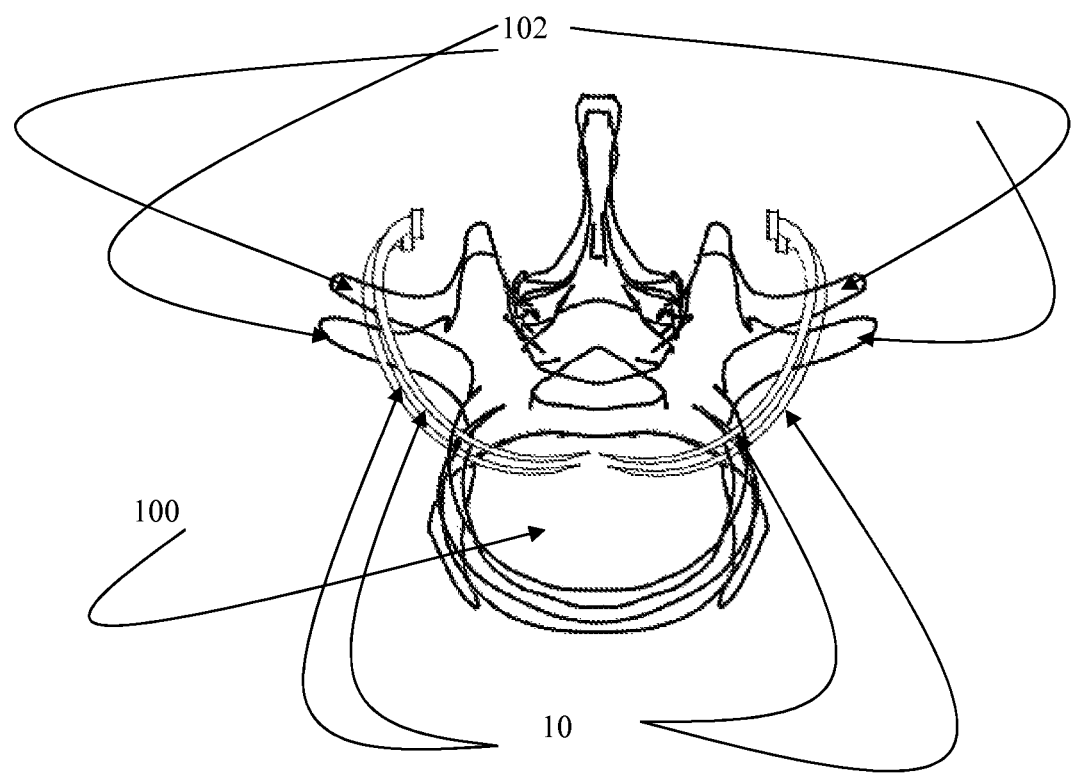
Figure 2D:
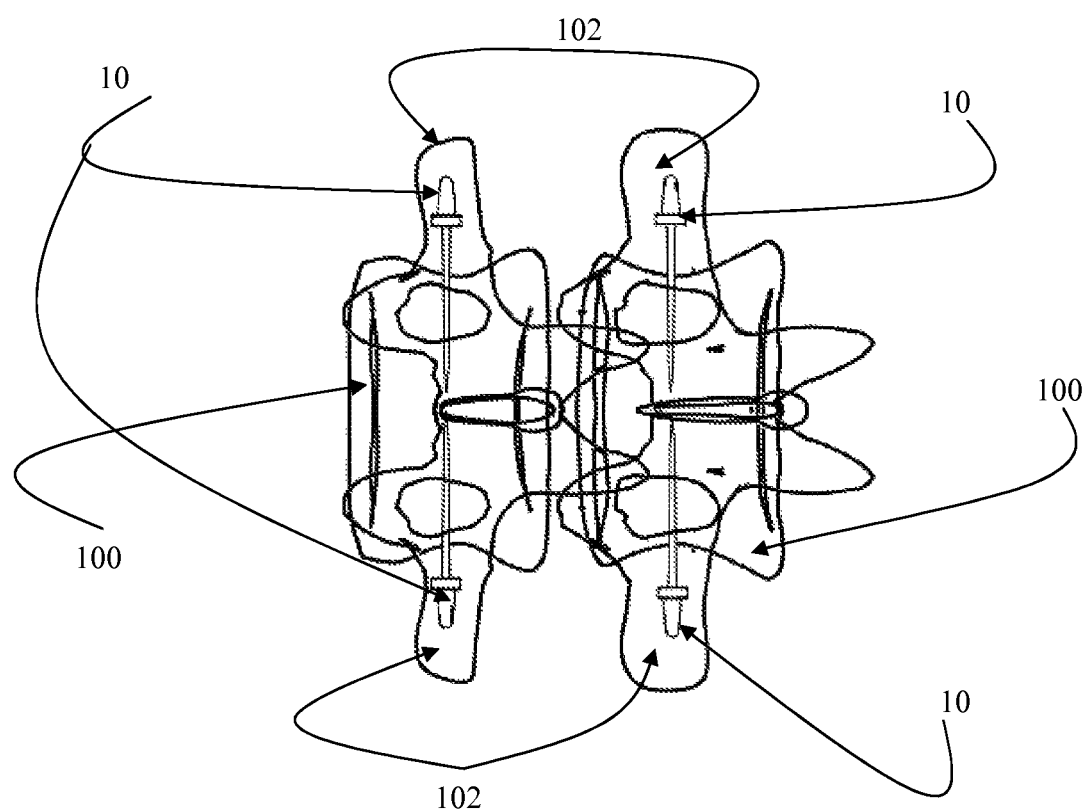
Figure 3A:
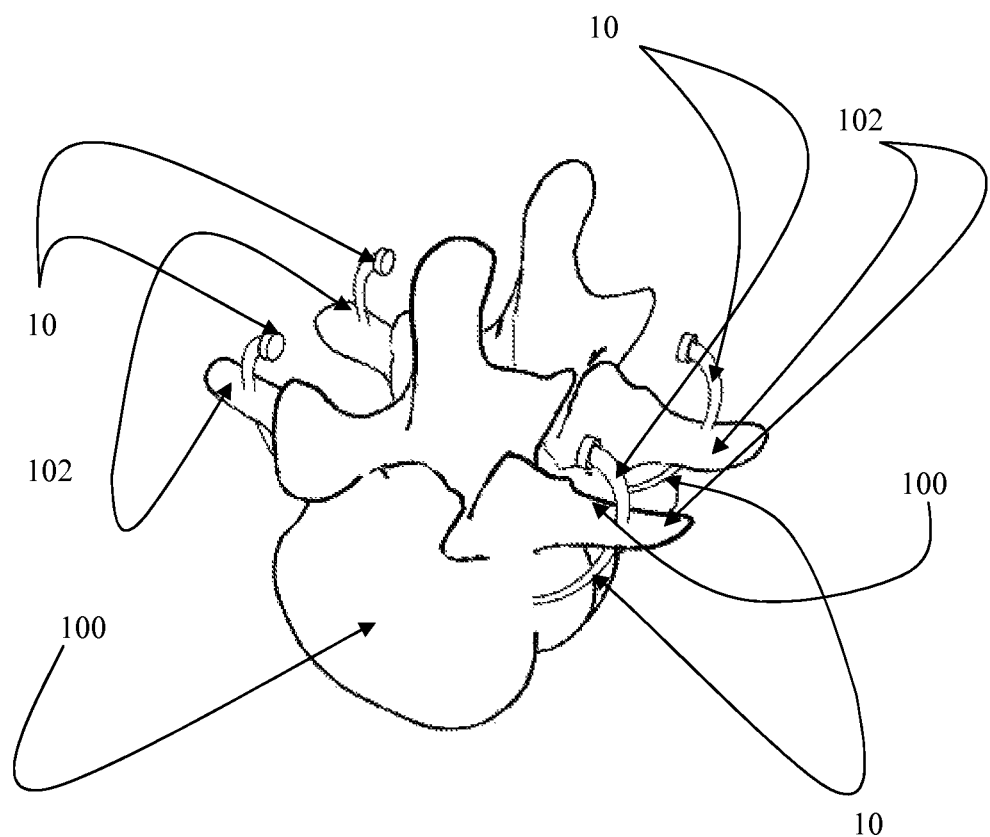
FIGS. 3A-D illustrate exemplary embodiments of an HTCN, embodiments (I-V), inserted bilaterally into two adjacent non-transparent vertebral bodies in top-oblique (Fig A), lateral (Figure B), axial (Figure C) and top (Figure D) views.
Figure 3B:
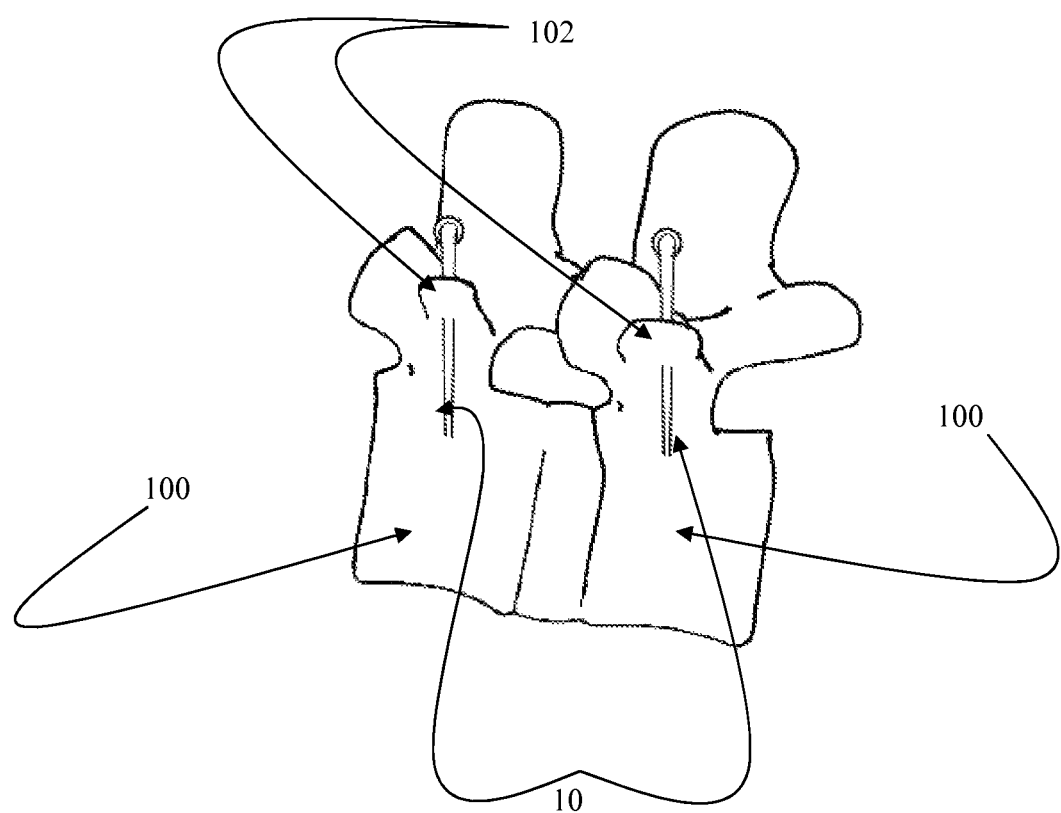
Figure 3C:
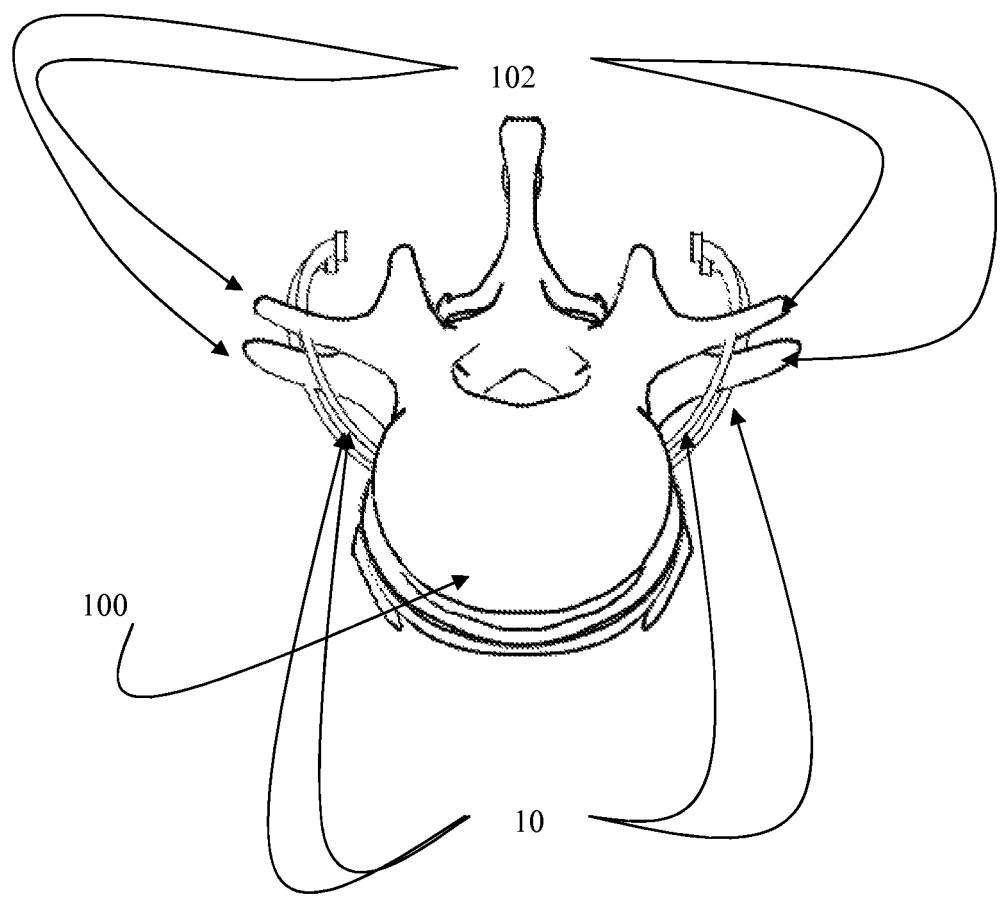
Figure 3D:
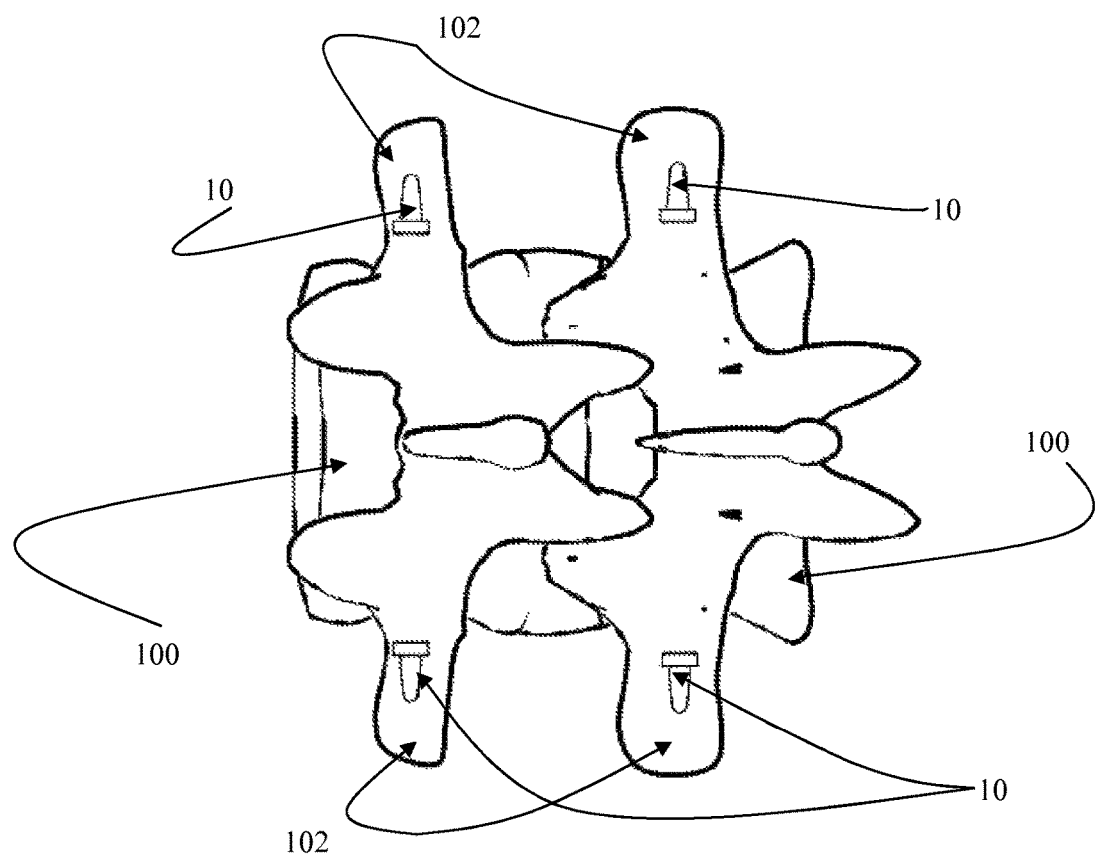
Figure 4A:
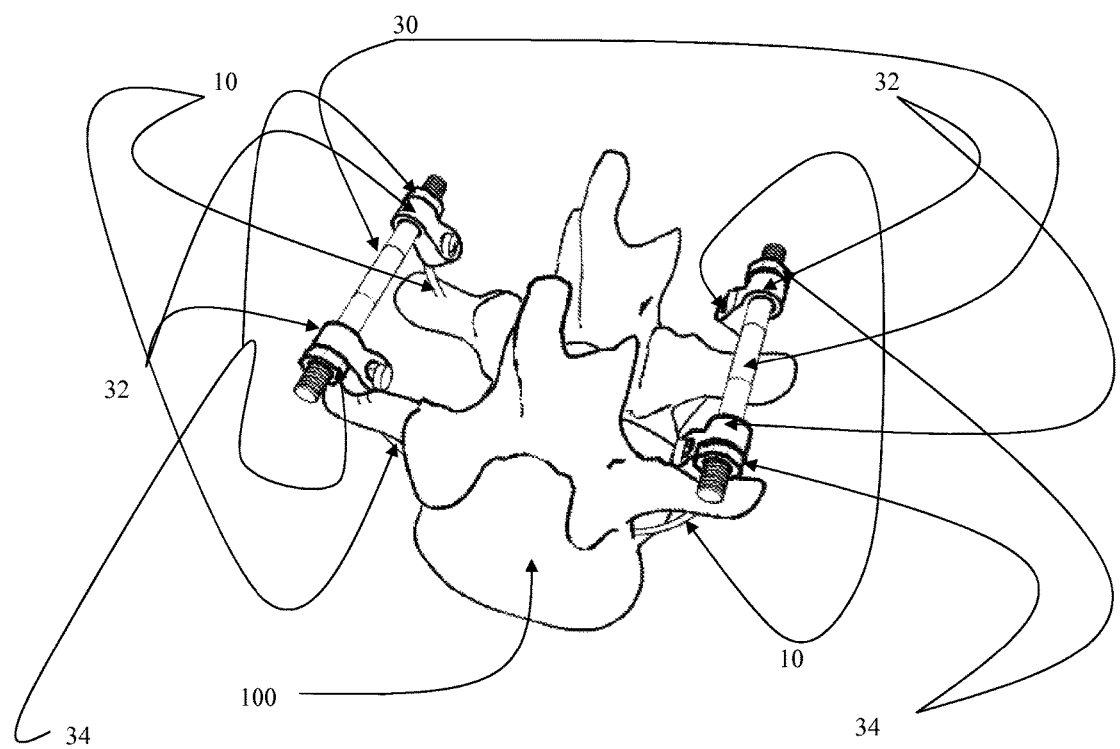
FIG. 4A illustrates exemplary embodiments of a rigid connecting rod-HTCN construct (Embodiment I) inserted bilaterally into two adjacent vertebral bodies in the superior oblique view
Figure 4B:
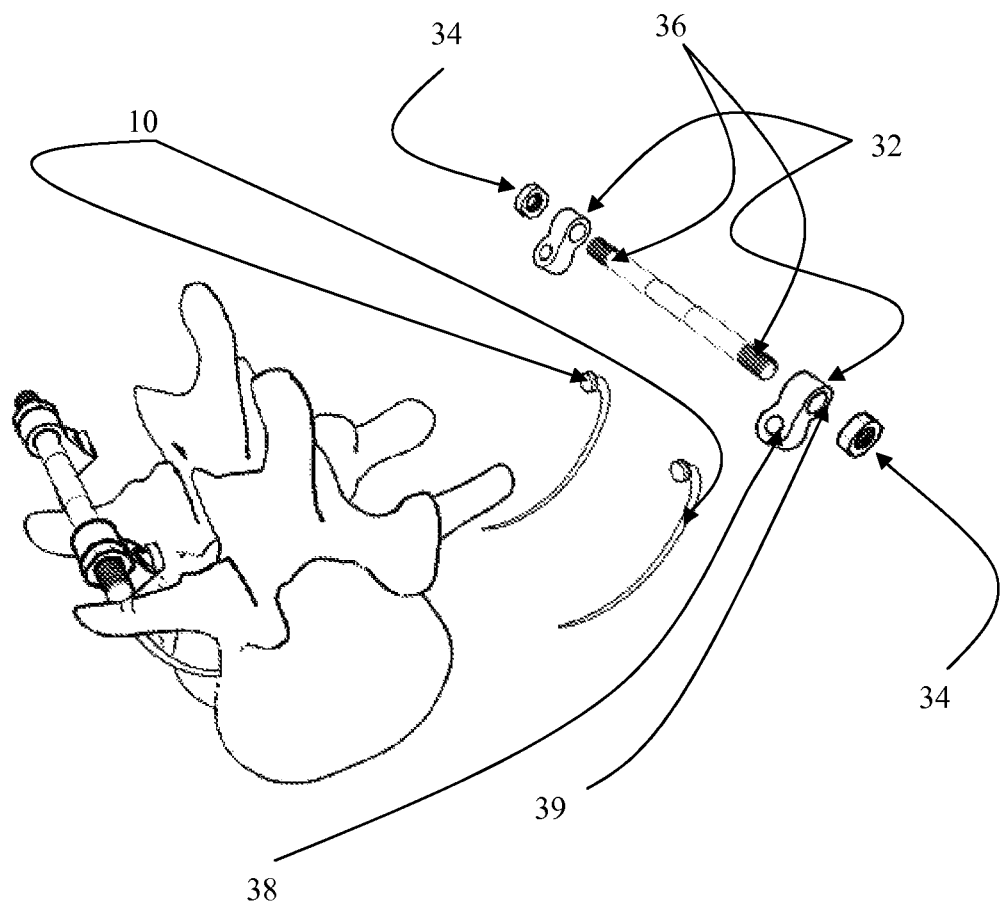
FIG. 4B illustrates an exploded view of the rigid connecting rod-HTCN construct (Embodiment I) of FIG. 4A.
Figure 4C:
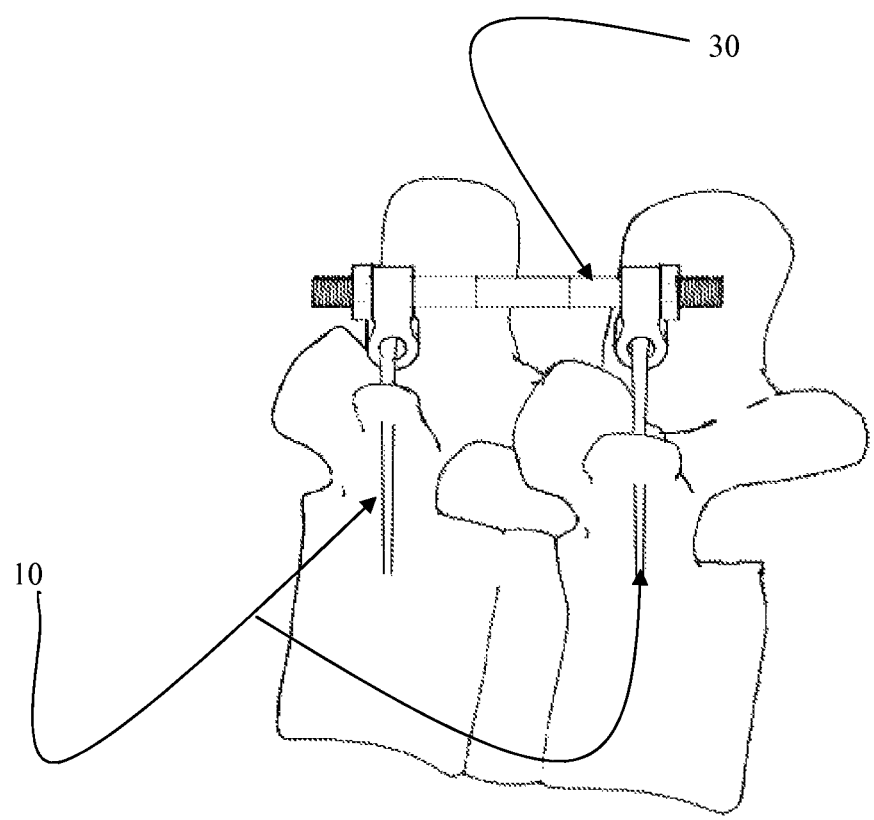
FIGS. 4C, D and E illustrate lateral (Figure C), axial (Figure D), and top (Figure E) view of exemplary embodiments of a rigid connecting rod-HTCN construct (Embodiment I) inserted bilaterally into two adjacent vertebral bodies.
Figure 4D:
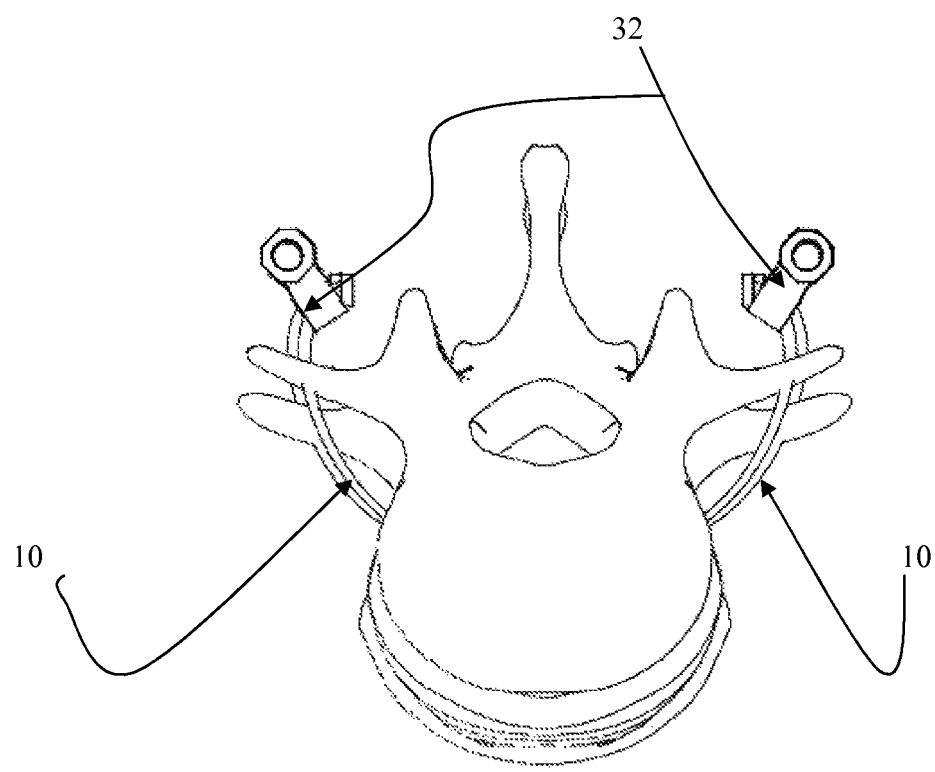
Figure 4E:
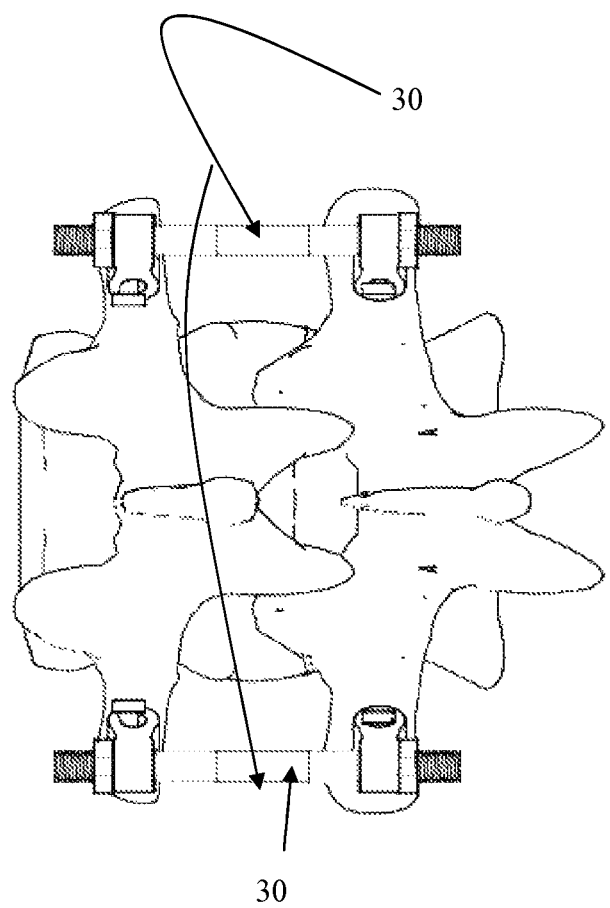

FIGS. 1G and H illustrate an exemplary embodiment of an HTCN 10 including a threaded tail-screw 22 (embodiment V). The threaded tail 22 can include threads 24 that can engage the cancellous core of the vertebral body. FIG. 1H is an enlargement illustrating details of an exemplary embodiment the threads 24.

Other variations and embodiments of the HTCN 10 can include any other type of mechanism that allows insertion and immobility of the HTCN 10 into and within the vertebral body (bodies).

The angle and geometric configuration of the HTCN 10 also can be altered or varied in multiple manners. The HTCN 10 also can be manufactured in varying sizes with respect to length and width providing a selection from which to choose to address different sized vertebral bodies in the same and/or different patients.

FIGS. 2A-D exemplarily illustrate the placement of a total of four HTCNs 10 into two adjacent transparent vertebral bodies in order to achieve their fusion, according to an exemplary method. A first HTCN 10 is inserted unilaterally into the right transparent vertebral body, a second HTCN 10 is inserted unilaterally into the left transparent vertebral body, a third HTCN 10 is inserted into the adjacent right transparent vertebral body, and a fourth HTCN 10 is inserted into the adjacent left transparent vertebral body. Two of the HTCNs 10 are lined up on the right, and two of the HTCNs 10 are lined up on the left. The initiating path of the curvilinear HTCNs 10 may begin posteriorly, laterally, or anteriorly, and the trajectory of the HTCN 10, for example, in all cases, is horizontal from its mid-lateral vertebral entry point to its final destination which is the relative inner center of the vertebral body. The HTCNs 10 are seen perforating the transverse processes. This is the estimated trajectory orientation for avoiding (e.g., necessary to avoid) exiting nerve roots. The entry point of the HTCN can be more medial, lateral, caudal or rostral to the transverse process. The initial position of insertion may be via a posterior, lateral or surgical approaches.

FIGS. 2A-D are transparent in order to appreciate the necessary HTCN trajectory, its position and orientation within the vertebrae, its entry point into the mid lateral vertebrae (FIG. 2B) and its starting and destination points.

FIGS. 3A-D exemplarily illustrate the placement of a total of four HTCNs 10 into two adjacent non-transparent vertebral bodies 100 in order to achieve fusion of these two adjacent bodies. A first HTCN 10 is inserted unilaterally into the right nontransparent vertebral body 100, a second HTCN 10 is inserted unilaterally into the left non-transparent vertebral body 100, a third HTCN 10 is inserted into the adjacent right non-transparent vertebral body 100, and a fourth HTCN 10 is inserted into the adjacent left non-transparent vertebral body 100. In the exemplary embodiment illustrated in FIGS. 3A-D, two of the HTCNs 10 are lined up on the right, and two of the HTCNs 10 are lined up on the left. The path of the curvilinear HTCNs 10 begins posteriorly, and its trajectory is horizontal from its entry point into the mid lateral vertebral body 100 to its final destination which is the relative center of the vertebral body 100.

The HTCNs 10 are illustrated as perforating the transverse processes 102. FIGS. 3A-D illustrate an example of an estimated trajectory and orientation for avoiding (e.g., necessary to avoid) exiting nerve roots. In other embodiments, the entry point of the HTCN 10 can be more medial, lateral, caudal, or rostral to the transverse process 102. The initial position of insertion may be via posterior, lateral, or anterior surgical approaches.

FIGS. 3A-D exemplarily illustrate how the HTCNs 10 may appear to the surgeon during a hypothetical operation.

FIGS. 4A-E exemplarily illustrate an example of a rigid connecting bar-HTCN construct (Embodiment I) that can achieve rigid segmental fusion of two adjacent vertebral bodies 100. This exemplary embodiment can include two HTCNs 10 coupled together. This connection can be rigid or fixed in at least one degree of movement, or more than one degree of movement. As illustrated in the exemplary embodiment, the HTCNs 10 can be coupled together by a rigid HTCN connecting bar 30, which can be threaded on either end, two connecting bar links 32, which can couple the bar 30 to each of the two HTCNs 10, and two tightening nuts 34 on the outsides of the connecting bar links 32, which can secure the connecting bar links 32 and bar 30 to the HTCNs 10. The connecting bar link 32 can include a first (upper) perforation (e.g., opening, through-hole, etc.) 39 that receives or engages a portion of the connecting bar 32, and a second (lower) perforation (e.g., opening, through-hole, etc.) 38 that receives or engages a portion of the HTCN 10, such as the head 16 of the HTCN 10. The HTCNs 10 are inserted into the second (lower) perforations 38 of the connecting bar link 32. In this manner, when the HTCNs 10 are secured to the vertebral bodies 100, each of the heads 16 of the HTCNs 10 is placed into a second (lower) perforation 38 of each of the two adjacent connecting bar links 32. This exemplary embodiment can include an HTCN 10 according to any of the exemplary embodiments (I-V) described above, as well as other arrangements.

The threaded rigid HTCN connecting bar 30 then can be implanted into the superior perforations (first or upper perforations) 39 of the connecting link 32 such that the threaded ends of the connecting bar 30 are disposed on the outside of the connecting links 32. A threaded tightening nut 34 can be secured to either or both ends of the connecting bar 30. In this manner, the exemplary embodiment can securely and effectively link two adjacent HTCNs 10 together in a rigid manner, thereby effectively achieving a rigid segmental fusion of two adjacent vertebrae.

FIGS. 4A-E exemplarily illustrate the implantation of these constructs into both the left and right sides of the spine.

The exemplary embodiment is illustrated with two HTCNs 10 per connecting bar 30. However, one or ordinary skill in the art will recognize that more than two HTCNs 10 can be coupled to each connecting bar 30. Furthermore, the threading on the connecting bar 30 is not limited to the illustrated embodiment and can extend along a portion or all of the length of the connecting bar 30. For example, in an alternative embodiment, three or more nuts 34 can be secured to the threaded connecting bar 30 to secure two or more connecting bar links 34 (e.g., three or four links 34, etc.) to the connecting bar 30, such that two or more HTCNs 10 (e.g., three or four HTCNs 10, etc.) can be coupled to the same connecting bar 30. The diameter of the connecting bar 30 is illustrated as being uniform along a length of the connecting bar 30. However, other embodiments are possible in which the diameter of the body of the connecting bar 30, the diameter of the threads, etc. can be different at different portions of the connecting bar 30. Other embodiments can include more than two connecting bar links 32, and more than two tightening nuts 34.

Figure 5A:
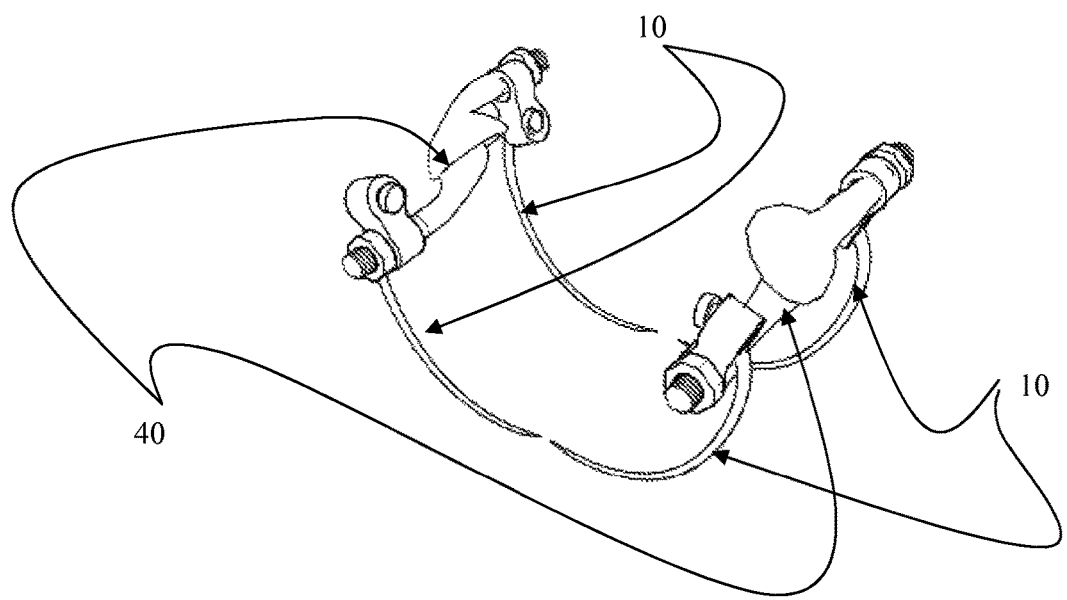
FIG. 5A illustrates exemplary embodiments of a ball-socket, side-side jointed connecting rod-HTCN construct (Embodiment II) in the superior-oblique view.
Figure 5B:
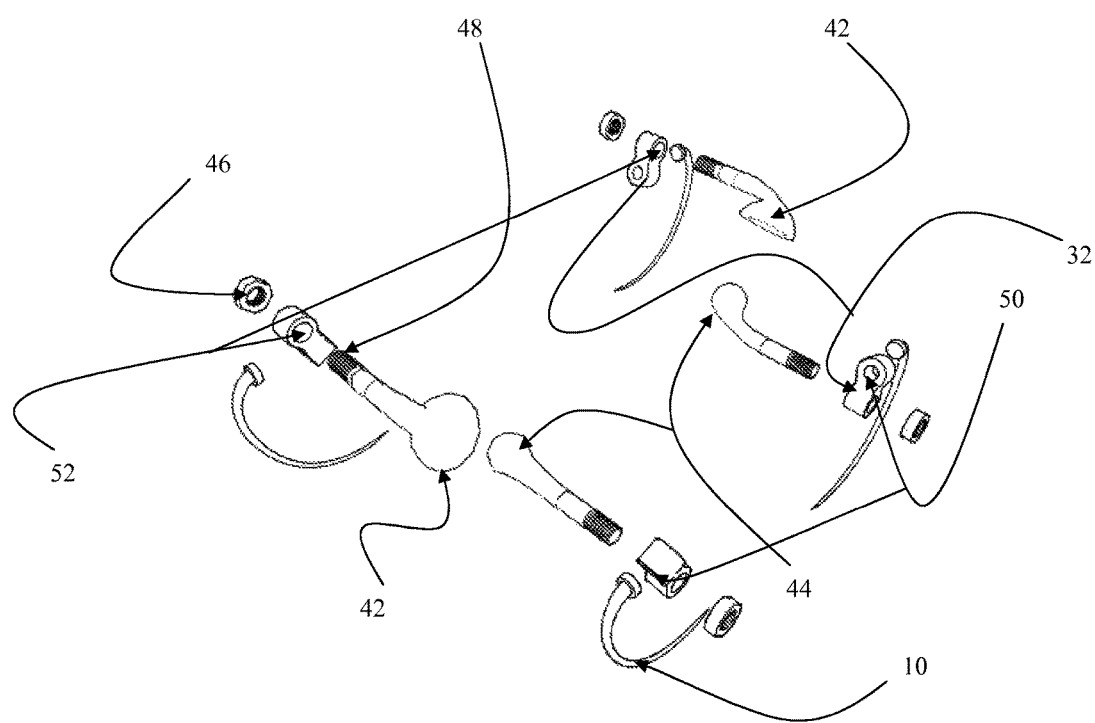
FIG. 5B illustrates an exploded view of the ball-socket, side-side jointed connecting rod-HTCN construct (Embodiment II) of FIG. 5A.
Figure 6A:
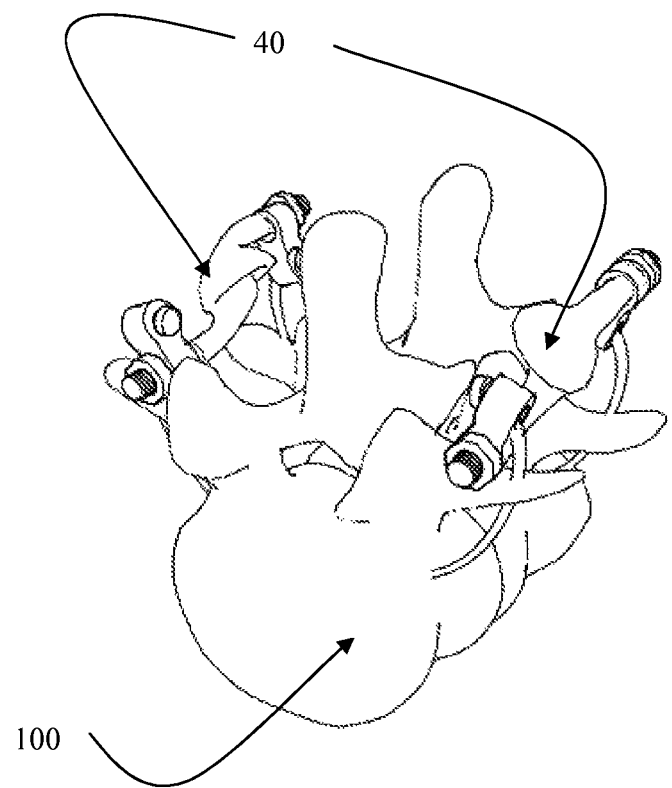
FIGS. 6A-D illustrate superior-oblique (Figure A), lateral (Figure B), axial (Figure C), and top (Figure D) view of exemplary embodiments of a ball-socket, side-side jointed connecting rod-HTCN construct inserted bilaterally into two adjacent vertebral bodies.
Figure 6B:
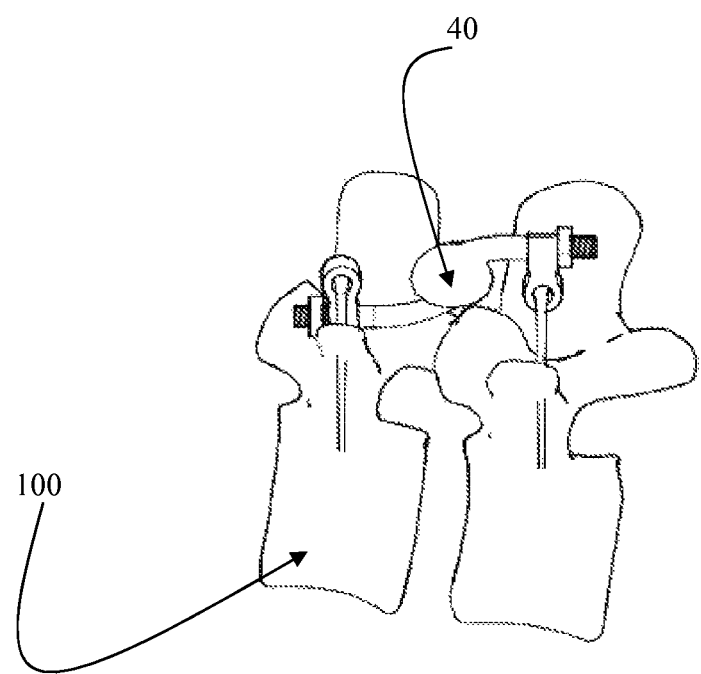
Figure 6C:
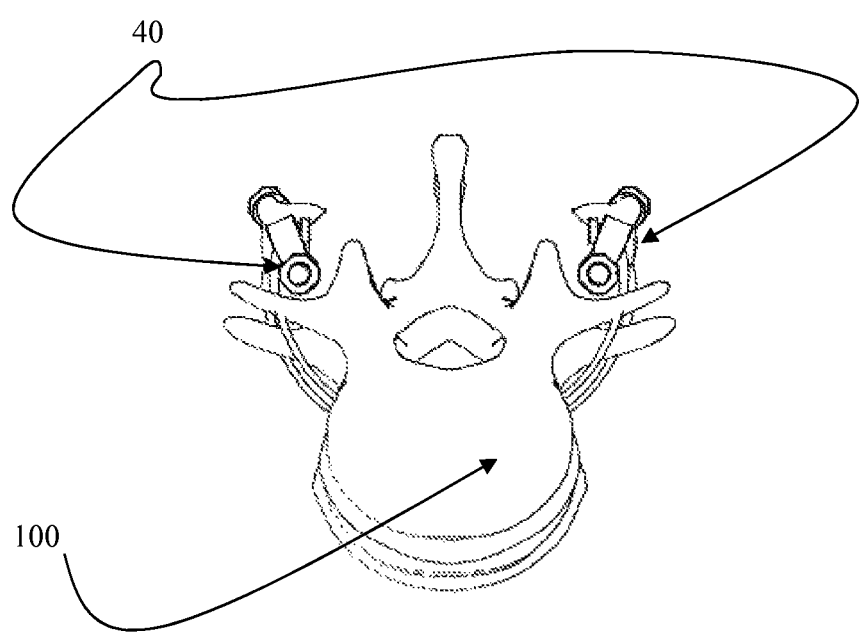
Figure 6D:
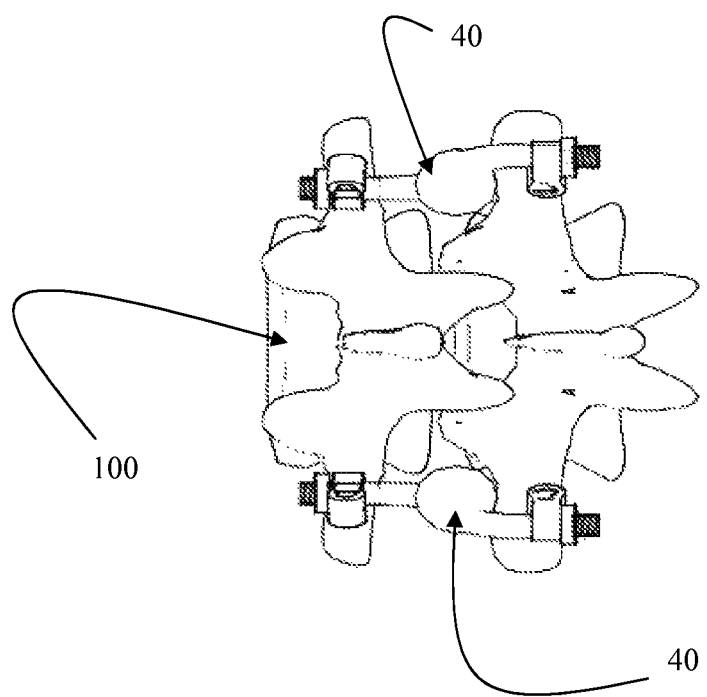

FIGS. 5A through 5B illustrate an exemplary embodiment of a plurality of HTCNs 10 coupled together with a flexible or movable connecting rod-HTCN construct (Embodiment II). For example, a ball and trough, side-side jointed connecting rod 40 can couple two or more HTCNs 10 together such that the HTCNs can move with respect to each other while being secured to each other. The connecting rod 40 can provide a flexible fusion or coupling (e.g., a movable coupling in at least one dimension) between the plurality of HTCNs 10.

In this embodiment, rather than using a horizontal rigid rod, such as the rod 30 in the embodiment illustrated in FIGS. 4A-E, the connecting rod 40 that connects two adjacent implanted HTCNs 10 can include two inter-locking components that allow for movement. The inter-locking components can include, for example: a) a first hemi-rod 44 having a distal end with a ball portion projecting from a side, and b) a second hemi-rod 42 having a distal end with an accepting trough (e.g. socket) projecting from its side. The first hemi-rod 44 can be coupled to the second hemi-rod 42 in a ball and socket manner.

The side to side interaction of the ball and trough components 44, 42 can provide a certain or predetermined degree of flexibility with motion or movement between the adjacent HTCNs 10 being coupled together. Hence, the exemplary embodiment can provide a flexible fusion or coupling between adjacent HTCNs 10.

This exemplary embodiment can include, for example, similar components as the embodiment I illustrated in FIGS. 4A-E. For example, two connecting bar links 32 and two or more tightening nuts 46 can be provided on either side of the two rod components 44, 42. The ends of the ball and trough rod components 44, 42 can be threaded 48 to receive or engage the nuts 46 to secure the connecting bar links 32 to the ball and trough rod components 44, 42, enable tightening of the constructs.

The connecting bar link 32 can include a first (superior, upper) perforation (e.g., opening, through-hole, etc.) 52 that receives or engages a portion of one of the rod components 44, 42, and a second (inferior, lower) perforation (e.g., opening, through-hole, etc.) 50 that receives or engages a portion of the HTCN 10, such as the head 16 of the HTCN 10. The HTCNs 10 are inserted into the second (inferior, lower) perforations 50 of the connecting bar link 32. In this manner, when the HTCNs 10 are secured to the vertebral bodies 100, each of the heads 16 of the HTCNs 10 is placed into a second (lower) perforation 50 of each of the two adjacent connecting bar links 32. This exemplary embodiment can include an HTCN 10 according to any of the exemplary embodiments (I-V) described above, as well as other arrangements.

The threaded portions or ends of each of the rod components 44, 42 can be inserted into the first (upper) perforations 52 of the connecting link 32 such that the threaded ends 48 of each of the rod components 44, 42 are disposed on the outside of the connecting links 32. A threaded tightening nut 46 can be secured to the end of each of the rod components 44, 42. In this manner, the exemplary embodiment can securely and effectively link two adjacent HTCNs 10 together in a flexible or moveable manner, thereby effectively achieving a flexible or moveable segmental fusion of two adjacent vertebrae.

FIGS. 6A-D exemplarily illustrate the ball and trough, side-side jointed connecting rod-HTCN construct (Embodiment II) that can provide a flexible fusion inserted bilaterally into adjacent vertebral bodies of the spine. Any of the five disclosed exemplary embodiments of the HTCN 10 (embodiments I-V), as well as other arrangements, may be selected for these constructs to insert into two adjacent vertebral bodies 100. Once this is done, the threaded, ball and trough, side-to-side jointed HTCN connecting bar 40 (rod components 44, 42) then can be implanted into the superior perforations (upper perforations) 52 of the connecting link 32, with at least a part of the threaded portions 48 of the rod components 44, 42 protruding outside these connecting links 32. Then the threaded tightening nuts 46 can be secured to either threaded end 48 of the rod components 44, 42 of the connecting bar 40. This construct effectively links two adjacent HTCNs 10 together in a non-rigid manner, effectively achieving flexible segmental fusion of two adjacent vertebrae.

FIGS. 6A-D exemplarily illustrate the implantation of these constructs into both the left and right sides of the spine.

The exemplary embodiment is illustrated with two HTCNs 10 per connecting bar 40. However, in alternative embodiments, more than two HTCNs 10 can be coupled to each connecting bar 40. Furthermore, the threading 48 on the connecting bar 40 is not limited to the illustrated embodiment. For example, in an alternative embodiment, three or more nuts 34 can be secured to the threaded connecting bar 40 to secure two or more connecting bar links 34 (e.g., three or four links 34, etc.) to the connecting bar 40, such that two or more HTCNs 10 (e.g., three HTCNs 10) can be coupled to the same connecting bar 40. Other embodiments can include more than two connecting bar links 32, and more than two tightening nuts 34.

Figure 7A:
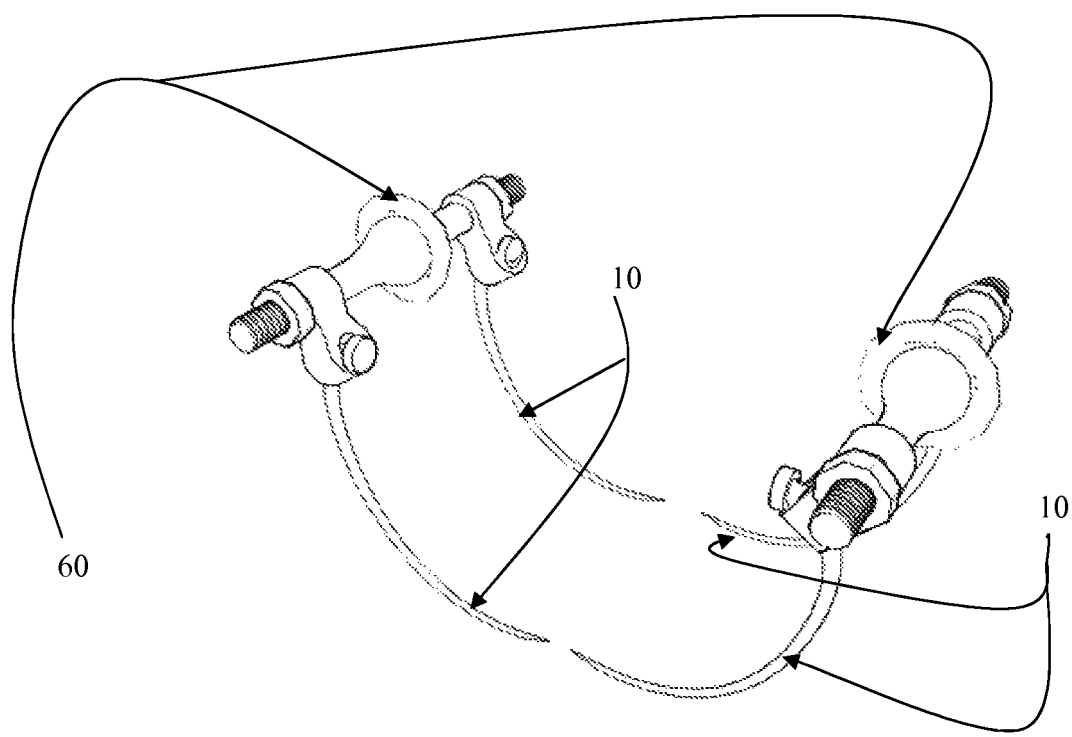
FIG. 7A illustrates exemplary embodiments of a ball-socket, head-head, jointed connecting rod-HTCN construct (Embodiment III) in the superior oblique view.

FIGS. 7A and B illustrate another exemplary embodiment of a plurality of HTCNs 10 coupled together with a ball and trough, head-to-head jointed connecting rod-HTCN construct (Embodiment III) to provide a flexible (or moveable) segmental fusion between the HTCNs 10.

For example, rather than using a horizontal rigid connecting rod 30, or a side-to-side ball and trough connecting rod 40, this exemplary embodiment includes a connecting rod 60 that connects two adjacent implanted HTCNs 10 and that includes two (a pair of) inter-locking components including, for example: a) a first hemi-rod 64 having a distal end including a ball projecting from its head, and b) a second hemi-rod 62 having a distal end including an accepting trough (or socket) projecting from its head.

This exemplary embodiment can include, for example, similar components as the embodiment I illustrated in FIGS. 4A-6D. The connecting rod 60 can include two connecting bar links 66 and two tightening nuts 70 on either side of the two rod components 64, 62 of the rod components 64, 62 of the connecting bar 60. The ends of the ball and trough head-head rod components 64, 62 can be threaded 68 to enable securing and tightening of the nuts 70 to the bar links 66, thereby securing the connecting bar links 66 to the ball and trough rod components 64, 62, enable tightening of the constructs.

The connecting bar link 66 can include a first (superior, upper) perforation (e.g., opening, through-hole, etc.) 74 that receives or engages a portion of one of the rod components 64, 62, and a second (inferior, lower) perforation (e.g., opening, through-hole, etc.) 72 that receives or engages a portion of the HTCN 10, such as the head 16 of the HTCN 10. The HTCNs 10 are inserted into the second (inferior, lower) perforations 72 of the connecting bar link 66. In this manner, when the HTCNs 10 are secured to the vertebral bodies 100, each of the heads 16 of the HTCNs 10 is placed into a second (lower) perforation 72 of each of the two adjacent connecting bar links 66. This exemplary embodiment can include an HTCN 10 according to any of the exemplary embodiments (I-V) described above, as well as other arrangements.

The threaded portions or ends 68 of each of the rod components 64, 62 can be inserted into the first (upper) perforations 74 of the connecting link 66 such that at least a portion of the threaded ends 68 of each of the rod components 64, 62 are disposed on the outside of the connecting links 66. A threaded tightening nut 70 can be secured to the threaded end 68 of each of the rod components 64, 62. In this manner, the head-head to side interaction of the ball and trough can enable or provide a certain (or predetermined) degree of flexibility with respect to motion between two adjacent and secured HTCNs 10, and hence, can provide a flexible fusion.

FIGS. 8A-D illustrate an exemplary embodiment of the ball and trough, head-head jointed connecting rod-HTCN construct (Embodiment III) that can provide a flexible fusion inserted bilaterally into the spine. Any of the five exemplary embodiments of the HTCN 10 (I-V) illustrated in FIGS. 1A-3D, as well as other arrangements, may be selected for these constructs to insert into two adjacent vertebral bodies 100. Once this is done, the threaded ball and trough, head-head jointed HTCN connecting bar 60 then can be implanted into the superior perforations 74 of the connecting link 66, with at least a portion of the threaded portion 68 of the rod components 64, 62 protruding outside the connecting links 66. Then, the threaded tightening nuts 70 can be secured to either threaded end 68 of the rod components 64, 62 of the connecting bar 60. This exemplary embodiment can provide a construct that effectively links two adjacent HTCNs 10 together in a non-rigid manner, effectively achieving flexible segmental fusion of two adjacent vertebrae.

FIGS. 8A-D exemplarily illustrate the implantation of these constructs into both the left and right sides of the spine.

All of the exemplary embodiments can be made of any biocompatible material, and can be manufactured in different sizes. The HTCNs 10 can be coupled together with various other interconnecting devices that can secured, either rigidly or non-rigidly, the HTCNs 10 together, and the embodiments are not limited to the exemplary embodiments illustrated in FIGS. 4A-8D.

2. Surgical Method

With reference again to FIGS. 1A-8D, exemplary methods and surgical steps for practicing one or more of the foregoing exemplary embodiments will now be described.

In practice, the HTCNs 10 are surgically implanted into two or more adjacent vertebrae, either unilaterally or bilaterally (see, e.g., FIGS. 2 and 3). The HTCNs 10 can be inserted using posterior, lateral, or anterior approaches. The HTCNs 10 can be inserted posterior through midline, or par midline approaches through opened, closed, endoscopic, or tubular techniques with or without fluoroscopic monitoring, or any other form of image guidance. The HTCNs 10 can be inserted through a lateral or anterior approach in likewise manner.

The surgeon can select an HTCN 10 according to any of the five HTCN embodiments (I-V) described herein, as well as other arrangements, for implantation (e.g., see FIG. 1A-H). Once two or more HTCNs 10 are inserted either unilaterally or bilaterally into adjacent vertebral bodies, then the surgeon can choose to connect two or more HTCNs 10 using, for example, the exemplary rigid HTCN connecting rod 30 for providing rigid segmental fusion (e.g., see FIG. 4). Alternatively, the surgeon can choose to connect one or more HTCNs 10 using, for example, (a) a flexible connecting rod 40 to form a ball and trough, side to side, jointed flexible rod-HTCN construct (embodiment II, FIGS. 5 and 6), or (b) a flexible connecting rod 60 to form a ball and trough, head to head, jointed flexible rod-HTCN construct (embodiment III), FIGS. 7 and 8.

The surgical procedure performed when choosing the rigid rod-HTCN construct (Embodiment I) begins with implantation of the HTCNs 10 into the lateral vertebral body 100 (e.g., FIGS. 2 and 3). One of the five embodiments of HTCNs 10, or other arrangements, can be chosen (e.g., FIG. 1A-H). Next, the HTCNs 10 can be tapped/screwed into the vertebral body 100 using a tamp and/or screw driver, or other suitable tool or device. Fluoroscopy/x-ray/image guidance can be used to confirm the entry point into the mid vertebral body, as well as the inner core mid-vertebral destination of the tapered end (pointed tip 14) of the HTCN 10. With posterior implantation, the pointed tip 14 of the HTCN 10 will often, but not necessarily always, traverse and perforate the transverse process (processes) 102 en route to its entry point into the mid-lateral vertebral body 100. Once two or more adjacent HTCNs 10 are successfully implanted into two adjacent vertebral bodies 100, then the heads 16 of the HTCN 10 can be placed into the inferior perforations 38 of two adjacent connecting bar links 32 (e.g., see FIGS. 4A-E).

The threaded rigid HTCN connecting bar 30 then can be inserted into the superior perforations 39 of the adjacent connecting bar links 32 with its threaded ends 36 protruding out of these links 32 (FIGS. 4A-E). Next, the threaded tightening nuts 34 can be secured to either threaded end 36 of the connecting bar 30. This construct effectively links two adjacent HTCNs 10 together in a rigid manner effectively achieving rigid fusion of two adjacent vertebrae. In other embodiments, the HTCN 10 can include a screw cap 16a, 16c that is fastened and tightened to a threaded portion 16b, 16d of the body 12 of the HTCN 10 to secure the head 16 of the HTCN to the inferior perforation 38 of the connecting rod link 32.

With reference to FIGS. 1A-3D and 5A-6D, exemplary methods and surgical steps for practicing one or more of the exemplary embodiments of flexible connecting bar constructs will now be described.

An example of a method or surgical procedure performed when choosing the flexible, ball and trough, side-side, rod-HTCN construct (Embodiment II) begins with implantation of the HTCNs 10 into the lateral vertebral body 100 (FIGS. 2 and 3). One of five exemplary embodiments of HTCNS 10, or other suitable arrangement, can be chosen (FIGS. 1A-H). Next, the HTCNs 10 can be tapped/screwed into the vertebral body 100 using a tamp and/or a screw driver, or other suitable tool or device. Fluoroscopy/x-ray/ image guidance can be used to confirm the entry point into the mid vertebral body, as well as the ultimate inner core mid-vertebral destination of the tapered end (pointed tip 14) of the HTCN 10. With posterior implantation, the pointed tip 14 of the HTCN 10 will often, but not always, traverse and perforate the transverse process (processes) 102 en route to the entry point of the HTCN 10 into the mid-lateral vertebral body 100. Other trajectories also can be used. Once two or more adjacent HTCNs 10 are successfully implanted into two adjacent vertebral bodies 100, then the heads 16 of the HTCN 10 can be placed into the inferior perforations 50 of two adjacent connecting bar links 36 (e.g., see FIGS. 5 and 6).

The threaded flexible HTCN connecting bar 40 is then inserted into the superior perforations 52 of the adjacent connecting bar links 32 with at least a portion of the threaded ends 48 protruding out of these links 32 (FIGS. 5 and 6). One hemi-rod (ball) 44 is inserted into one connecting link 32, and the other hemi-rod (trough) 42 is inserted into the adjacent connecting link 32. The placement of the ball 44 against the trough 42 can be optimized for flexibility. Next, the threaded tightening nuts 46 are secured to either of the threaded ends 48 of the rod components 44, 42 of the hemi-connecting bars 40. These exemplary constructs can effectively link two adjacent HTCNs 10 together in a flexible manner effectively achieving rigid fusion of two adjacent vertebrae. With respect to the HTCN embodiments with screw caps 16a, 16c, once the construct is created, the screw caps 16a, 16c can be fastened and tightened to the superior ends 16b, 16d of the body 12 of the HTCNs 10 which protrude from outside the inferior perforations 50 of the connecting bar links 32, thereby securing the head 16 of the HTCN 10 to the inferior perforation 50 of the connecting bar link 32.

With reference to FIGS. 1A-3D and 7A-8D, exemplary methods and surgical steps for practicing one or more of the exemplary embodiments of flexible connecting bar constructs will now be described.

An example of a method or surgical procedure performed when choosing the flexible, ball and trough, head-head, rod-HTCN construct (Embodiment III) begins with implantation of the HTCNs 10 into the lateral vertebral body 100 (FIGS. 2 and 3). One of five exemplary embodiments of HTCNs 10, or other suitable arrangements, can be chosen (FIGS. 1A-H). Next, the HTCNs 10 are tapped/screwed into the vertebral body 100 using a tamp and/or a screw driver, or other suitable tool or device. Fluoroscopy/x-ray/navigational image guidance can be used to confirm the entry point into the mid vertebral body, as well as the ultimate inner core mid-vertebral destination of the tapered end (pointed tip 14) of the HTCN 10. With posterior implantation, the pointed tip 14 of the HTCN 10 will often, but not always, traverse and perforate the transverse process (processes) 102 en route to its entry point into the mid-lateral vertebral body 100. Other trajectories also can be used. Once two or more adjacent HTCNs 10 are successfully implanted into two adjacent vertebral bodies 100, then the heads 16 of the HTCN 10 are placed into the inferior perforations 72 of two adjacent connecting bar links 66 (e.g., see FIGS. 7 and 8).

Figure 7B:
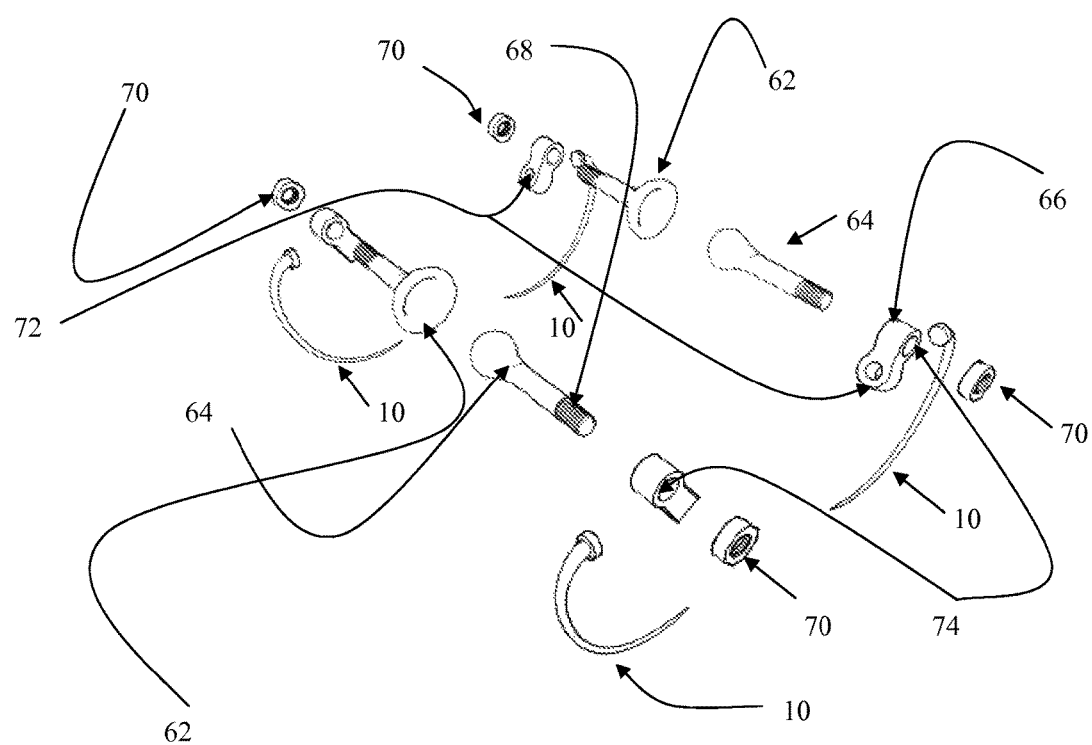
FIG. 7B illustrates an exploded view of the ball-socket, head-head jointed connecting rod-HTCN construct (Embodiment III) of FIG. 7A.
Figure 8A:
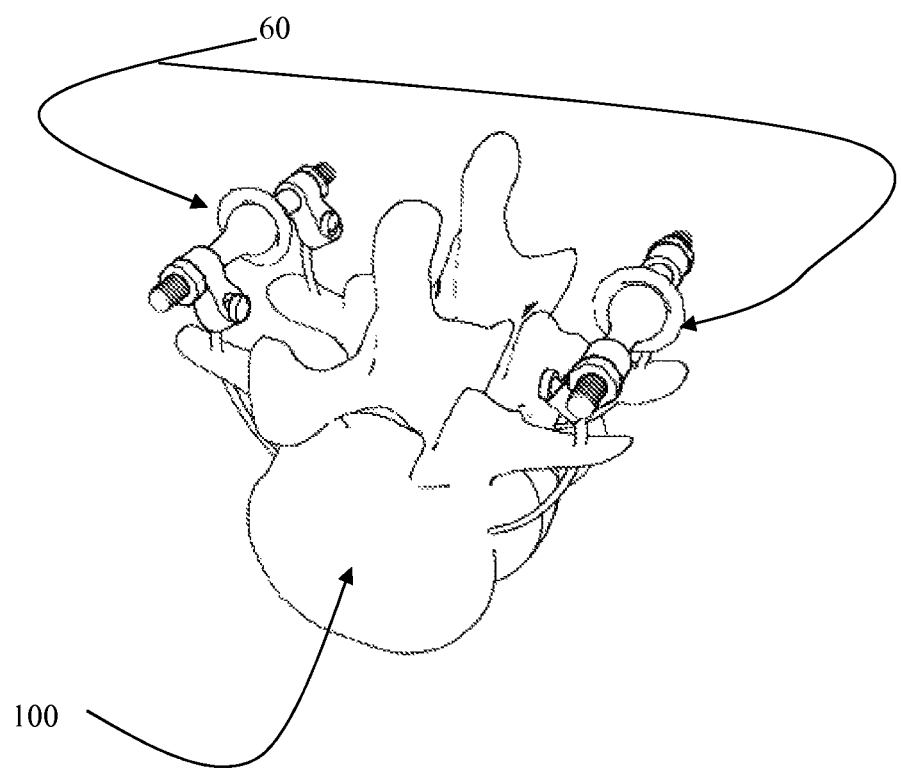
FIGS. 8A-D illustrate the superior-oblique (Figure A), lateral (Figure B), axial (Figure C), and top (Figure D) views of exemplary embodiments of a ball-socket, head-head jointed connecting rod-HTCN construct inserted bilaterally into two adjacent vertebral bodies.
Figure 8B:
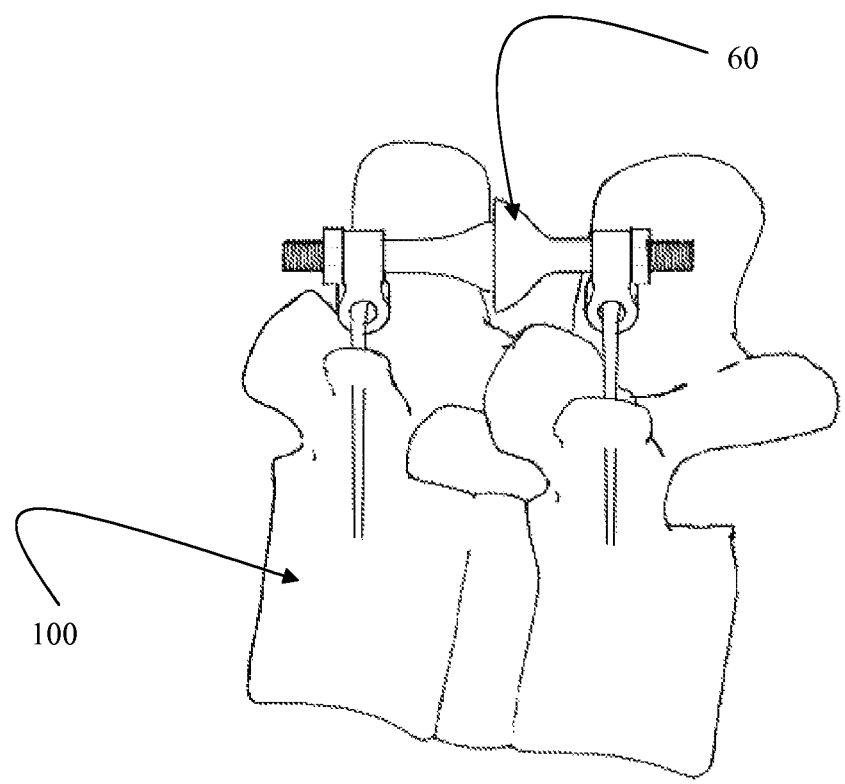
Figure 8C:
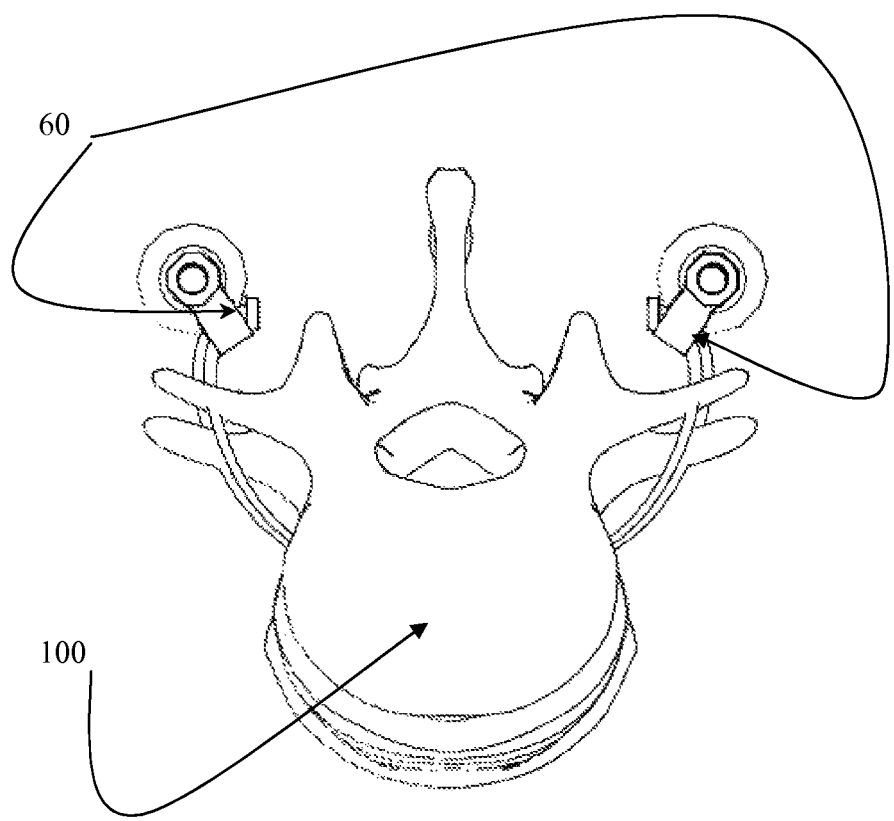
Figure 8D:
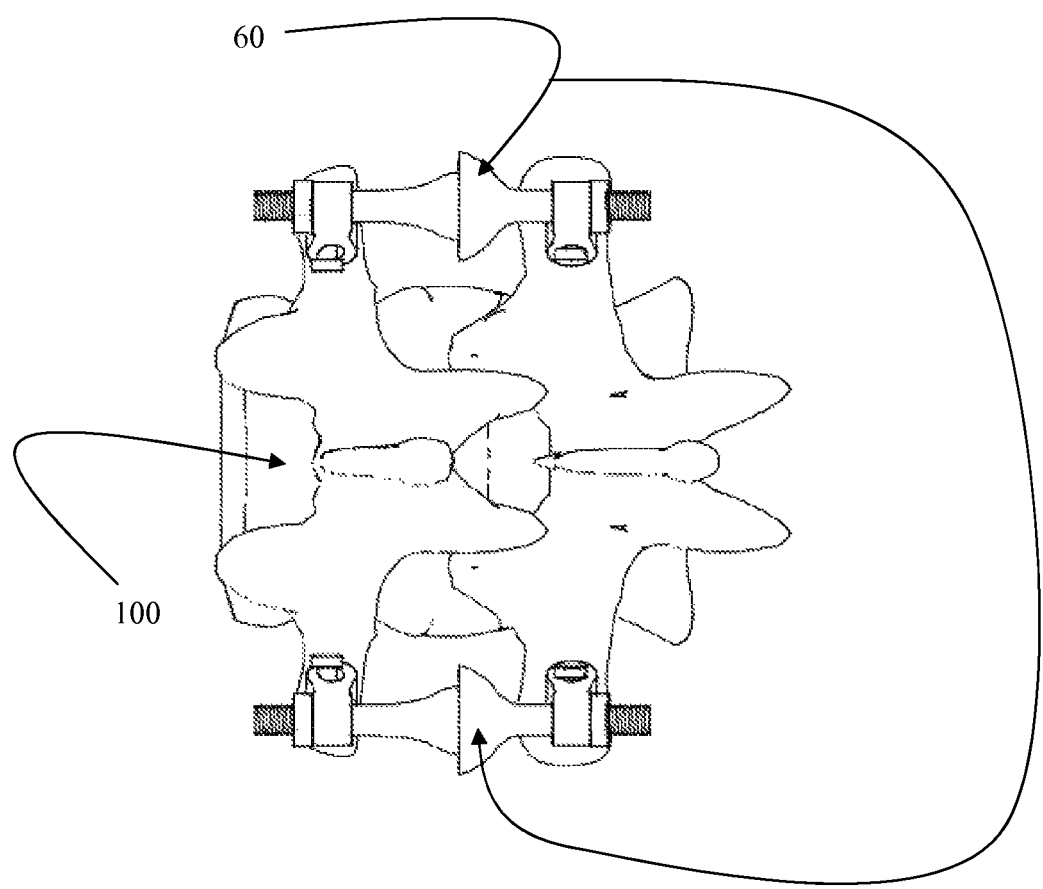

The threaded flexible HTCN connecting bar 60 is then inserted into the superior perforations 74 of the adjacent connecting bar links 66 with at least a portion of the threaded ends 68 protruding out of these links 66 (FIGS. 7 and 8). One hemi-rod (ball) 64 is inserted into one connecting link 66, and the other hemi-rod (trough) 62 is inserted into the adjacent connecting link 66. The placement of the ball 64 against the trough 62 can be optimized for flexibility. Next, the threaded tightening nuts 70 can be secured to either threaded end 48 of the rod components 64, 62 of the hemi-connecting bar 60. This exemplary construct can effectively link two adjacent HTCNs 10 together in a flexible manner effectively achieving flexible segmental fusion of two adjacent vertebrae. With respect to the HTCN embodiments with screw caps 16a, 16c, once the construct is created, the screw caps 16a, 16c can be fastened and tightened to the superior ends 16c, 16d of the HTCNs 10 which protrude from outside the inferior perforations 72 of the connecting bar links 66, thereby securing the head 16 of the HTCN 10 to the inferior perforation 72 of the connecting rod link 66.

The exemplary embodiments of the Horizontal Curvilinear Transvertebral Nail-screws (HTCNs) described herein can provide a segmental vertebral spinal fusion that has a strength that is equal to or greater than a strength provided by conventional pedicle screws without the complications arising from pedicle screw placement, which can include, for example, misplacement with potential nerve and/or vascular injury, violation of healthy facets, and possible pedicle destruction. By placing the exemplary HTCNs 10 horizontally across the vertebral body, and not into the vertebral bodies via the transpedicular route thereby excluding the posterior spinal column, then healthy facet joints and pedicles can be preserved. The exemplary HTCNs 10 can include predetermined curved angles to avoid laterally exiting nerve roots. Furthermore, with respect to patients who already have had pedicle screws, with concomitant pedicular destruction, the placement of the exemplary HTCNs 10 can be employed as a salvage procedure achieving segmental fixation without, for example, having to engage additional rostral and caudal vertebrae transpedicularly, unnecessarily lengthening a spinal fusion, and adding more operative risk per fused level.

Furthermore, because of the orientation and length of the exemplary HTCNs, multiple level fusions can be easily performed.

The present invention has been described herein in terms of several preferred embodiments. However, modifications and additions to these embodiments will become apparent to those of ordinary skill in the art upon a reading of the foregoing description. It is intended that all such modifications and additions comprise a part of the present invention to the extent that they fall within the scope of the several claims appended hereto.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper", "lateral", "left", "right" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. The device may be otherwise oriented (rotated 90 degrees or at other orientations) and the descriptors of relative spatial relationships used herein interpreted accordingly.

What is claimed is:

1. A spinal fusion implant comprising:
a first curvilinear nail-screw for penetration and implantation into a first vertebral body along a first curved trajectory that avoids penetrating pedicles, wherein the first curvilinear nail screw extends from a first proximal end to a first distal end along the first curved trajectory with a first head at the first proximal end and a first bone penetrating pointed tip at the first distal end, wherein the first curvilinear nail-screw comprises first means for engaging a first cancellous core of the first vertebral body positioned along a first distal portion of the first curvilinear nail-screw proximate the first distal end, wherein the first curved trajectory is along a first single continuous arc;
a second curvilinear nail-screw for penetration and implantation into a second vertebral body along a second curved trajectory that avoids penetrating pedicles, wherein the second curvilinear nail screw extends from a second proximal end to a second distal end along the second curved trajectory with a second head at the second proximal end and a second bone penetrating pointed tip at the second distal end, wherein the second curvilinear nail-screw comprises second means for engaging a second cancellous core of the second vertebral body positioned along a second distal portion of the second curvilinear nail-screw proximate the second distal end, wherein the second curved trajectory is along a second single continuous arc; and
a connecting support structure defining a first hole sized and configured for receiving the first curvilinear nail screw and a second hole sized and configured for receiving the second curvilinear nail screw such that the first curvilinear nail-screw is held with respect to the second curvilinear nail-screw with the first curvilinear nail-screw extending into the first vertebral body without penetrating pedicles and the second curvilinear nail-screw extending into the second vertebral body without penetrating pedicles.

2. The spinal fusion implant of claim 1, and further comprising first and second rotatable connectors configured for retaining the first and second curvilinear nail-screws to the connecting support structure.

3. The spinal fusion implant of claim 1, wherein the first means for engaging a first cancellous core of the first vertebral body and the second means for engaging a second cancellous core of the second vertebral body comprise radially arranged fish-hooks.

4. The spinal fusion implant of claim 1, wherein the first means for engaging a first cancellous core of the first vertebral body and the second means for engaging a second cancellous core of the second vertebral body comprise threads.

5. The spinal fusion implant of claim 1, wherein the first curvilinear nail-screw comprises a first smooth portion between the first head and the first distal portion and wherein the second curvilinear nail-screw comprises a second smooth portion between the second head and the second distal portion, and wherein the first means for engaging a first cancellous core of the first vertebral body and the second means for engaging a second cancellous core of the second vertebral body each comprise one or more ridges.

6. The spinal fusion implant of claim 1, wherein the connecting support comprises at least first and second separate components, wherein the first component defines the first hole for the first curvilinear nail screw, and wherein the first component is connected directly to the second component.

7. The spinal fusion implant of claim 6, wherein the connecting support comprise a third component that defines the second hole for the second curvilinear nail screw and wherein the third component is connected directly to the second component.

8. The spinal fusion implant of claim 1, wherein the connecting support structure is a bar.

9. The spinal fusion implant of claim 1, wherein the first and second curvilinear nail-screws are oriented by the connecting support structure to be introduced laterally into the first and second vertebral bodies.

10. The spinal fusion implant of claim 1, wherein the first and second curvilinear nail-screws are oriented by the connecting support structure to be introduced posteriorly into the first and second vertebral bodies.

11. The spinal fusion implant of claim 1, wherein the first and second curvilinear nail-screws are oriented by the connecting support structure to be introduced anteriorly into the first and second vertebral bodies.

12. The spinal fusion implant of claim 1, wherein the first and second heads comprise first and second caps.

13. The spinal fusion implant of claim 1, wherein the connecting support structure is sized and configured to be positioned exterior to the first and second vertebral bodies when connecting the first and second curvilinear nail-screws while the first and second curvilinear nail-screws penetrate into the first and second vertebral bodies.

14. The spinal fusion implant of claim 1, wherein the first curvilinear nail-screw shares a first centerline axis with the first hole where the first curvilinear nail-screw extends through the first hole and wherein the second curvilinear nail-screw shares a second centerline axis with the second hole where the second curvilinear nail-screw extends through the second hole.

15. The spinal fusion implant of claim 1, wherein the first and second curvilinear nail-screws connect to the first and second holes of the support structure at curved portions of the first and second curvilinear nail-screws.

16. The spinal fusion implant of claim 1, wherein the first curvilinear nail-screw is curved from the first proximal end to the first distal end including a portion of the first curvilinear nail-screw connected to the connecting support structure and the second curvilinear nail-screw is curved from the second proximal end to the second distal end including a portion of the second curvilinear nail-screw connected to the connecting support structure.

17. A method of implanting a spinal fusion implant, the method comprising:
   implanting a first curvilinear nail-screw to penetrate into a first vertebral body along a first curved trajectory that avoids pedicles, wherein the first curvilinear nail screw extends from a first proximal end to a first distal end along the first curved trajectory with a first head at the first proximal end and a first bone penetrating pointed tip at the first distal end, wherein the first curvilinear nail-screw comprises first means for engaging a first cancellous core of the first vertebral body positioned along a first distal portion of the first curvilinear nail-screw proximate the first distal end, wherein the first head is positioned exterior to the first vertebral body and the first distal portion is positioned in the first cancellous core when implanted, wherein the first curved trajectory is along a first single continuous arc;
   implanting a second curvilinear nail-screw to penetrate into a second vertebral body along a second curved trajectory that avoids pedicles, wherein the second curvilinear nail screw extends from a second proximal end to a second distal end along the second curved trajectory with a second head at the second proximal end and a second bone penetrating pointed tip at the second distal end, wherein the second curvilinear nail-screw comprises second means for engaging a second cancellous core of the second vertebral body positioned along a second distal portion of the second curvilinear nail-screw proximate the second distal end, wherein the second head is positioned exterior to the second vertebral body and the second distal portion is positioned in the second cancellous core when implanted, wherein the second curved trajectory is along a second single continuous arc;
   connecting the first curvilinear nail-screw to the second curvilinear nail-screw via a connecting support structure such that the first curvilinear nail-screw is held with respect to the second curvilinear nail-screw with the first curvilinear nail-screw extending into the first vertebral body without penetrating pedicles and the second curvilinear nail-screw extending into the second vertebral body without penetrating pedicles.

18. The method of claim 17, wherein the first curvilinear nail-screw penetrates into the first vertebral body so as to traverse no more than 50% of the first vertebral body and the second curvilinear nail-screw penetrates into the second vertebral body so as to traverse no more than 50% of the second vertebral body.

19. The method of claim 17, wherein the first and second curvilinear nail-screws penetrate into the first and second vertebral bodies without traversing an intervertebral disk.

20. The method of claim 17, wherein the first means for engaging a first cancellous core of the first vertebral body and the second means for engaging a second cancellous core of the second vertebral body comprise radially arranged fish-hooks.

21. The method of claim 17, wherein the first means for engaging a first cancellous core of the first vertebral body and the second means for engaging a second cancellous core of the second vertebral body comprise threads.

22. The method of claim 17, wherein the first and second curvilinear nail-screws are introduced laterally into the first and second vertebral bodies.

23. The method of claim 17, wherein the first and second curvilinear nail-screws are introduced anteriorly into the first and second vertebral bodies.

* * * * *